United States Patent
Buie et al.

(10) Patent No.: US 12,007,350 B2
(45) Date of Patent: Jun. 11, 2024

(54) DEVICES, SYSTEMS, AND METHODS FOR MEASURING A SOLUTION CHARACTERISTIC OF A SAMPLE COMPRISING MICROORGANISMS

(71) Applicant: Avails Medical, Inc., Menlo Park, CA (US)

(72) Inventors: Creighton T. Buie, Daly City, CA (US); Hima Shah, Sunnyvale, CA (US); Nitin K. Rajan, Palo Alto, CA (US); Ashraf M. Wahba, Hayward, CA (US); Oren S. Knopfmacher, San Francisco, CA (US); Meike Herget, Woodside, CA (US)

(73) Assignee: Avails Medical, Inc., Menlo Park, CA (US)

(*) Notice: Subject to any disclaimer, the term of this patent is extended or adjusted under 35 U.S.C. 154(b) by 0 days.

(21) Appl. No.: 18/057,622

(22) Filed: Nov. 21, 2022

(65) Prior Publication Data
US 2023/0090007 A1   Mar. 23, 2023

Related U.S. Application Data

(60) Division of application No. 17/117,780, filed on Dec. 10, 2020, now Pat. No. 11,536,682, which is a
(Continued)

(51) Int. Cl.
*G01N 27/30* (2006.01)
*B01L 3/00* (2006.01)
(Continued)

(52) U.S. Cl.
CPC .......... *G01N 27/301* (2013.01); *B01L 3/5023* (2013.01); *G01N 27/125* (2013.01);
(Continued)

(58) Field of Classification Search
CPC .. G01N 27/301; G01N 27/302; G01N 27/125; G01N 27/4167; G01N 27/4168;
(Continued)

(56) References Cited

U.S. PATENT DOCUMENTS 3,461,055 A * 8/1969 Staunton .............. G01N 27/301
                                                       204/435
3,530,056 A   9/1970 Haddad
(Continued)

FOREIGN PATENT DOCUMENTS

GB        1568644 A  *  6/1980  ......... G01N 27/4035
JP     2003-287515       10/2003
(Continued)

OTHER PUBLICATIONS

Gamry, ParaCell Electrochemical cell kit, Jun. 13, 2013. (Year: 2013).

*Primary Examiner* — Luan V Van
*Assistant Examiner* — Shizhi Qian
(74) *Attorney, Agent, or Firm* — Levine Bagade Han LLP

(57) ABSTRACT

Various apparatus, systems, and methods for measuring a solution characteristic of a sample comprising microorganisms are disclosed. In one embodiment, a sensor apparatus is disclosed comprising a sample container comprising a sample chamber configured to receive the sample and a reference sensor component comprising a reference conduit having a reference conduit cavity defined therein. The reference conduit cavity can be at least partially filled with a reference buffer gel, buffer solution, or wicking component. A segment of the reference conduit can extend into the sample chamber. A reference electrode material can be positioned at a proximal end of the wicking component or extend partially into the reference conduit cavity. The sensor apparatus can also comprise an active sensor component having an active electrode in fluid contact with the sample.

(Continued)

The sample in the sample chamber can be aerated through an aeration port defined along a surface of the sample container.

13 Claims, 17 Drawing Sheets

Related U.S. Application Data continuation of application No. PCT/US2019/037915, filed on Jun. 19, 2019.

(60) Provisional application No. 62/687,167, filed on Jun. 19, 2018.

(51) Int. Cl.
 *G01N 27/12* (2006.01)
 *G01N 27/416* (2006.01)

(52) U.S. Cl.
 CPC ....... *G01N 27/302* (2013.01); *G01N 27/4167* (2013.01); *G01N 27/4168* (2013.01); *B01L 2300/042* (2013.01); *B01L 2300/0645* (2013.01); *B01L 2300/161* (2013.01); *B01L 2300/165* (2013.01)

(58) Field of Classification Search
 CPC .............. G01N 33/5438; B01L 3/5023; B01L 2300/042; B01L 2300/0645; B01L 2300/161; B01L 2300/165; B01L 2300/0681; B01L 2300/0829
 See application file for complete search history.

(56) References Cited

U.S. PATENT DOCUMENTS

| | | | |
|---|---|---|---|
| 4,632,746 A | 12/1986 | Bergman | |
| 4,891,125 A * | 1/1990 | Schultz | G01N 27/301 |
| | | | 264/267 |
| 5,470,453 A | 11/1995 | Nipkow et al. | |
| 8,128,989 B1 * | 3/2012 | Millar | G01N 27/333 |
| | | | 205/787.5 |
| 11,536,682 B2 | 12/2022 | Buie et al. | |
| 2002/0189944 A1 * | 12/2002 | Connelly | G01N 27/401 |
| | | | 204/435 |
| 2004/0106190 A1 | 6/2004 | Yang et al. | |
| 2004/0134779 A1 | 7/2004 | Hsu et al. | |
| 2005/0191481 A1 * | 9/2005 | He | A61L 9/037 |
| | | | 428/304.4 |
| 2006/0027453 A1 | 2/2006 | Catalano et al. | |
| 2009/0026078 A1 * | 1/2009 | Wolf | G01N 27/4035 |
| | | | 204/433 |
| 2011/0004077 A1 | 1/2011 | Leichner et al. | |
| 2011/0048971 A1 | 3/2011 | Bower et al. | |
| 2011/0070655 A1 | 3/2011 | Horiuchi et al. | |
| 2013/0295660 A1 | 11/2013 | Fey | |
| 2016/0047824 A1 | 2/2016 | Dilleen et al. | |
| 2016/0116427 A1 * | 4/2016 | Laurenson | B05D 5/00 |
| | | | 427/2.13 |
| 2017/0113221 A1 | 4/2017 | Hoffman et al. | |
| 2017/0261464 A1 | 9/2017 | Shi et al. | |
| 2017/0342459 A1 | 11/2017 | Knopfmacher et al. | |
| 2021/0131993 A1 | 5/2021 | Buie et al. | |

FOREIGN PATENT DOCUMENTS

| | | | |
|---|---|---|---|
| JP | 2009-075127 | 4/2009 | |
| JP | 2010-517032 | 5/2010 | |
| JP | 2013/127455 | 6/2013 | |
| JP | 2013-127455 | 6/2013 | |
| WO | WO 2009/055092 | 4/2009 | |
| WO | WO-2009055092 A1 * | 4/2009 | ........... G01N 27/401 |
| WO | WO 2019/246208 | 12/2019 | |
| WO | WO 2002/030220 | 4/2022 | |

\* cited by examiner

DEVICES, SYSTEMS, AND METHODS FOR MEASURING A SOLUTION CHARACTERISTIC OF A SAMPLE COMPRISING MICROORGANISMS

CROSS-REFERENCE TO RELATED APPLICATIONS

This application is a divisional of U.S. patent application Ser. No. 17/117,780 filed on Dec. 10, 2020, which is a continuation of PCT Application No. PCT/US2019/037915 filed on Jun. 19, 2019, which claims the benefit of U.S. Provisional Application No. 62/687,167 filed on Jun. 19, 2018, the entirety of which is incorporated herein by reference.

TECHNICAL FIELD

The present disclosure relates generally to diagnostic devices for measuring a solution characteristic of a sample; more specifically, to devices, systems, and methods for measuring a solution characteristic of a sample comprising microorganisms.

BACKGROUND

Infections caused by anti-infective resistant infectious agents or microbes are a significant problem for healthcare professionals in hospitals, nursing homes, and other healthcare environments. For example, such infections can lead to a potentially life-threatening complication known as sepsis where chemicals released into the bloodstream by an infectious agent can trigger a dangerous whole-body inflammatory response as well as a vasoactive response causing fever, low blood pressure, and possibly death. When faced with such an infection, a preferred course of action is for a clinician to use anti-infective compounds judiciously, preferably only those necessary to alleviate the infection.

However, what occurs most frequently today is that until the organism is identified and tested for drug sensitivity, broad spectrum anti-infectives, often multiple drugs, are given to the patient to ensure adequacy of treatment. This tends to result in multiple drug resistant infectious agents. Ideally, the sensitivity of the infectious agent would be detected soon after its presence is identified. In order to determine the susceptibility of such infectious agents to anti-infectives, samples comprising such infectious agents must be quantified, which requires such samples to be assayed for microbial growth or lack thereof.

Existing biosensors used to assay infectious agents in biological samples or other types of samples often include an active sensing component having an active electrode and a reference sensing component having a reference electrode immersed in a reference solution that is in ion exchange contact with the sample of interest. Traditionally, this is accomplished using an Ag/AgCl electrode in an aqueous reference buffer solution like KCl. However, this traditional sensor design is not ideal for various reasons. First, silver or silver chloride can diffuse into the sample and inhibit the growth of microorganisms in the sample, thus complicating any measurements done on the sample. Moreover, traditional reference solutions are often provided in a thin glass-walled disposable container, which is costly to manufacture, store, and transport. Furthermore, microbial diffusion through the salt bridge formed between the sample and the reference solution can contaminate the reference solution. In addition, traditional biosensors often required the reference electrode to be positioned on the silicon die surface, which used valuable wafer real estate and further increased the cost of such sensors.

As a result of the above limitations and restrictions, there is a need for improved devices, systems, and methods to quickly and effectively assay a sample comprising microorganisms for microbial growth or lack thereof. Such a solution should be cost-effective and address the shortcomings of traditional biosensors.

SUMMARY

Disclosed are apparatus, systems, and methods for measuring a solution characteristic (e.g., an ORP or pH) of a sample comprising microorganisms. In one embodiment, a sensor apparatus for measuring a solution characteristic of a sample is disclosed. The sensor apparatus can comprise a sample container comprising a sample chamber configured to receive the sample and a reference sensor component. The reference sensor component can comprise a reference conduit comprising a reference conduit cavity, a reference conduit first opening, and a reference conduit second opening. The reference sensor component can also comprise a wicking component extending through the reference conduit cavity having a wick distal end and a wick proximal end. At least part of the wicking component can be in fluid communication with the sample chamber such that at least some of the sample is drawn by the wicking component in a direction of the wick proximal end. The reference sensor component can also comprise a reference electrode material disposed at the wick proximal end.

The sensor apparatus can further comprise an active sensor component comprising an active electrode material. At least part of the active electrode material can extend into the sample chamber and be in fluid contact with the sample when the sample chamber is filled, at least partially, with the sample.

The reference sensor component and the active sensor component can be electrically coupled by conductive connections to a parameter analyzer. The solution characteristic of the sample can be determined based on a potential difference measured between the active electrode material and the reference electrode material.

The sensor apparatus can comprise a container cap configured to be removably coupled to the sample container. The reference conduit can extend from an underside of the container cap. The container cap can be made in part of a non-conducting material. The container cap can be made in part of a transparent non-conducting material such that at least part of the wicking component is visible through the container cap.

The sample container can be made in part of at least one of a ceramic material and a polymeric material. The reference electrode material can be an electrically-conductive ink applied or dispensed on the wick proximal end. The electrically-conductive ink applied or dispensed on the wick proximal end can be hardened by curing. In some embodiments, the electrically-conductive ink can be a silver-silver chloride ink.

The wicking component can be made in part of a porous polymeric material. In some embodiments, the wicking component can be made in part of high density polyethylene (HDPE). In other embodiments, the wicking component can be made in part of natural fibers. The wicking component can comprise pores sized between about 15 μm to about 150 μm.

The wicking component can be treated by a surfactant such that at least a surface of the wicking component can be covered by the surfactant. The surfactant can be configured to increase a hydrophilicity of the wicking component.

The sensor apparatus can further comprise an aeration port defined along at least one of a bottom side and a lateral side of the sample container. In some embodiments, a hydrophobic air-permeable membrane can cover the aeration port. The aeration port and the hydrophobic air-permeable membrane can be configured to allow air to enter the sample chamber through the aeration port and the hydrophobic air-permeable membrane to aerate the sample chamber.

When the reference sensor component is implemented as a container cap, the container cap can be configured to be removably coupled to the sample container via an attachment connection and an additional hydrophobic air-permeable membrane can cover at least part of an underside of the container cap. In these embodiments, an airflow pathway can be created when the container cap is screwed on to the sample container via the attachment connection (e.g., a threaded connection). The airflow pathway can include the aeration port, the hydrophobic air-permeable membrane, the sample chamber, the additional hydrophobic air-permeable membrane, and air gaps defined in between the container cap and the sample container along the attachment connection.

In some embodiments, the solution characteristic measured by the sensor apparatus is pH and the active electrode material of the active sensor component can be made in part of a pH-sensitive material. In some embodiments, the pH-sensitive material comprises at least one of silicon dioxide, aluminum oxide, titanium dioxide, tantalum pentoxide, hafnium dioxide, iridium dioxide, ruthenium dioxide, and zirconium dioxide.

In other embodiments, the solution characteristic measured can be an oxidation reduction potential (ORP) of the sample and the active electrode material of the active sensor component can be made in part of a redox-sensitive material. The redox-sensitive material can comprise at least one of platinum, gold, silicon dioxide, aluminum oxide, titanium dioxide, tantalum pentoxide, hafnium dioxide, iridium dioxide, ruthenium dioxide, and zirconium dioxide. In these and other embodiments, the parameter analyzer can be or comprise at least part of a voltmeter and a multimeter.

Also disclosed is a reference sensor component. The reference sensor component can be configured to removably couple to a sample container configured to receive a sample. The reference sensor component can also comprise a reference conduit comprising a reference conduit cavity. In some embodiments, the reference sensor component can be implemented as a container cap. The reference conduit can extend from an underside of the container cap.

The reference sensor component can comprise a wicking component disposed within part of the reference conduit cavity having a wick distal end and a wick proximal end. At least part of the wicking component can be configured to be in fluid contact with the sample when the container cap is coupled to the sample container such that at least some of the sample is drawn by the wicking component in a direction of the wick proximal end. The reference sensor component can also comprise a reference electrode material disposed at the wick proximal end. The reference electrode material can be configured to exhibit a substantially stable electrode potential compared to an active electrode in electrical communication with the reference electrode material.

The reference sensor component can be made in part of a non-conducting material. When the reference sensor component is implemented as a container cap, the container cap can be made in part of a non-conducting material. In certain embodiments, the container cap can be made in part of a transparent non-conducting material such that at least part of the wicking component is visible through the container cap.

In some embodiments, the reference electrode material can be an electrically-conductive ink applied or dispensed on the wick proximal end. The electrically-conductive ink applied or dispensed on the wick proximal end can be hardened by curing. In some embodiments, the electrically-conductive ink can be a silver-silver chloride ink.

The wicking component can be made in part of a porous polymeric material. In other embodiments, the wicking component can be made in part of natural fibers. The wicking component can comprise pores sized between about 15 μm to about 150 μm.

The wicking component can be treated by a surfactant such that at least a surface of the wicking component is covered by the surfactant. The surfactant can be configured to increase a hydrophilicity of the wicking component.

Disclosed is also a method of measuring a solution characteristic of a sample. The method can comprise filling a sample chamber of a sample container with a sample comprising an infectious agent, attaching a reference sensor component (e.g., implemented as a container cap) to the sample container, electrically coupling a reference electrode material of the reference sensor component to a parameter analyzer and electrically coupling the parameter analyzer to an active sensor component comprising an active electrode material, and determining the solution characteristic of the sample based on a potential difference measured between the active electrode material and the reference electrode material.

At least part of the active electrode material can extend into the sample chamber and is in fluid contact with the sample. The reference sensor component can comprise a reference conduit comprising a reference conduit cavity, a reference conduit first opening, and a reference conduit second opening. The reference conduit cavity can be filled in part by a wicking component extending through the reference conduit cavity having a wick distal end and a wick proximal end.

At least part of the wicking component can be in fluid contact with the sample within the sample chamber. At least some of the sample can be drawn by the wicking component (e.g., by capillary action) in a direction of the wick proximal end.

The reference electrode material can be disposed at the wick proximal end. The reference electrode material can be an electrically-conductive ink applied or dispensed on the wick proximal end. The electrically-conductive ink can be hardened by curing. In some embodiments, the electrically-conductive ink can be a silver-silver chloride ink.

The method can further comprise pumping air into the sample chamber through an aeration port defined along at least one of a bottom side and a lateral side of the sample container and a hydrophobic air-permeable membrane covering the aeration port, wherein the air pumped into the sample chamber aerates the sample. The air pumped into the sample chamber can exit the sample chamber through an additional air-permeable membrane covering at least part of an underside of the container cap and through air gaps defined in between the container cap and the sample container along an attachment connection.

The step of determining the solution characteristic of the sample can comprise determining the pH of the sample. The active electrode material can be made in part of a pH-sensitive material. In some embodiments, the pH-sensitive material can comprise at least one of silicon dioxide, aluminum oxide, titanium dioxide, tantalum pentoxide, hafnium dioxide, iridium dioxide, ruthenium dioxide, and zirconium dioxide.

In other embodiments, the step of determining the solution characteristic of the sample can comprise determining an oxidation reduction potential (ORP) of the sample and wherein the active electrode material is made in part of a redox-sensitive material. The redox-sensitive material can comprise at least one of platinum, gold, silicon dioxide, aluminum oxide, titanium dioxide, tantalum pentoxide, hafnium dioxide, iridium dioxide, ruthenium dioxide, and zirconium dioxide.

A method of manufacturing a reference sensor component is disclosed. The method can comprise providing a container cap configured to be removably coupled to a sample container configured to receive a sample. A reference conduit can extend from an underside of the container cap. The reference conduit can comprise a reference conduit cavity. The method can also comprise positioning a wicking component into the reference conduit cavity. The wicking component can comprise a wick distal end and a wick proximal end. The method can further comprise applying or dispensing an electrically-conductive ink on the wick proximal end and curing the electrically-conductive ink until the electrically-conductive ink hardens.

The method can further comprise applying or dispensing, on the wick proximal end, a volume of the electrically-conductive ink between about 50 μL and 500 μL. The electrically-conductive ink can be cured at a temperature above 100° C. The electrically-conductive ink can be cured for a period of time between about 60 minutes and about 180 minutes.

In some embodiments, the reference conduit can be tapered. The wicking component can be shaped such that the wicking component tapers from the wick proximal end to the wick distal end.

Disclosed herein is another embodiment of a sensor apparatus for measuring a pH of a sample. The sensor apparatus can comprise a sample container comprising a sample chamber configured to receive the sample and a reference sensor component.

The reference sensor component can comprise a reference conduit comprising a reference conduit cavity, a reference conduit first opening and a reference conduit second opening. In some embodiments, the reference conduit cavity can be at least partially filled with a reference buffer gel. A segment of the reference conduit can extend into the sample chamber. The reference conduit second opening can be configured to allow the sample to be in fluid contact with the reference buffer gel. A reference electrode can extend partially into the reference conduit cavity filled with the reference buffer gel.

The sensor apparatus can further comprise an active sensor component comprising an active electrode housing extending into the sample chamber and an active electrode housed partially within the active electrode housing. The active electrode can comprise a sample contact surface.

The active electrode can be disposed at a distal end of the active electrode housing. The active electrode housing can be configured to expose the sample contact surface such that the sample contact surface is in fluid communication with the sample.

A conductive contact layer can be coupled to the active electrode and positioned proximal to the active electrode within the active electrode housing. The conductive contact layer and the reference electrode can be electrically coupled by conductive connections to a voltmeter. The pH of the sample can be measured based on a potential difference between the active electrode and the reference electrode.

The reference conduit can comprise conduit walls. The conduit walls can taper from a reference conduit proximal end to a reference conduit distal end such that a first opening area of the reference conduit first opening is larger than a second opening area of the reference conduit second opening.

The reference electrode can comprise a reference electrode tip. The reference electrode tip can be positioned proximal to the reference conduit second opening when the reference electrode is partially extended into the reference conduit cavity such that a volume of reference buffer gel separates the reference electrode tip from the reference conduit second opening. The reference conduit cavity can be filled with about 100 μL to about 500 μL of reference buffer gel.

The reference electrode can be made in part of one or more metals. In some embodiments, the reference electrode can be made in part of platinum, stainless steel, or a combination thereof.

The active electrode can be made in part of a metal oxide. In some embodiments, the active electrode can be made in part of silicon dioxide, aluminum oxide, titanium dioxide, tantalum pentoxide, hafnium dioxide, iridium dioxide, ruthenium dioxide, zirconium dioxide, or a combination thereof.

The conductive contact layer can be made in part of one or more metals. The conductive contact layer can be made in part of aluminum, copper, platinum, or a combination thereof.

In some embodiments, the reference buffer gel can be an agar gel formed from agar powder and a reference buffer solution. The agar powder in the agar gel can be at a concentration of about 1% (w/v %) to about 5% (w/v %).

The reference buffer solution can comprise potassium hexacyanoferrate(III), potassium hexacyanoferrate(II), potassium dihydrogen phosphate, disodium hydrogen phosphate, or a combination thereof. In other embodiments, the reference buffer solution can comprise potassium chloride.

The sensor apparatus can comprise an aeration conduit. A segment of the aeration conduit can extend into the sample chamber. The aeration conduit can be configured to aerate the sample within the sample container.

Also disclosed is another embodiment of a sensor apparatus for measuring an oxidation-reduction potential (ORP) of a sample. The sensor apparatus can comprise a sample container comprising a sample chamber configured to receive the sample and a reference sensor component.

The reference sensor component can comprise a reference conduit comprising a reference conduit cavity, a reference conduit first opening and a reference conduit second opening. The reference conduit cavity can be at least partially filled with a reference buffer gel. A segment of the reference conduit can extend into the sample chamber.

The reference conduit second opening can be configured to allow the sample to be in fluid contact with the reference buffer gel. A reference electrode can extend partially into the reference conduit cavity filled with the reference buffer gel.

The sensor apparatus can further comprise an active sensor component. The active sensor component can comprise an active electrode housing extending into the sample chamber and an active electrode housed partially within the active electrode housing. The active electrode can comprise a sample contact surface. The active electrode can be disposed at a distal end of the active electrode housing and the active electrode housing can be configured to expose the sample contact surface such that the sample contact surface is in fluid communication with the sample. The active electrode and the reference electrode can be electrically coupled by conductive connections to a voltmeter. The ORP of the sample can be measured based on a potential difference between the active electrode and the reference electrode.

The reference conduit can comprise conduit walls. The conduit walls can taper from a reference conduit proximal end to a reference conduit distal end such that a first opening area of the reference conduit first opening is larger than a second opening area of the reference conduit second opening. The reference conduit cavity can be filled with about 100 µL to about 500 µL of reference buffer gel.

The reference electrode can comprise a reference electrode tip. The reference electrode tip can be positioned proximal to the reference conduit second opening when the reference electrode is partially extended into the reference conduit cavity such that a volume of reference buffer gel separates the reference electrode tip from the reference conduit second opening.

The reference electrode can be made in part of one or more metals. In some embodiments, the reference electrode can be made in part of platinum, stainless steel, or a combination thereof.

The active electrode can be made in part of one or more metals, one or more metal oxides, or a combination thereof. For example, the active electrode can be made in part of platinum, gold, silicon dioxide, aluminum oxide, titanium dioxide, tantalum pentoxide, hafnium dioxide, iridium dioxide, ruthenium dioxide, zirconium dioxide, or a combination thereof.

The reference buffer gel can be an agar gel formed from agar powder and a reference buffer solution. The agar powder in the agar gel can be at a concentration of about 1% (w/v %) to about 5% (w/v %).

The reference buffer solution can comprise potassium hexacyanoferrate(III), potassium hexacyanoferrate(II), potassium dihydrogen phosphate, disodium hydrogen phosphate, or a combination thereof. In other embodiments, the reference buffer solution can comprise potassium chloride.

The sensor apparatus can further comprise an aeration conduit or aeration port. A segment of the aeration conduit can extend into the sample chamber. The aeration conduit can be configured to aerate the sample within the sample container.

Also disclosed is another embodiment of a sensor apparatus for measuring a pH of a sample. The sensor apparatus comprising a sample container comprising a sample chamber configured to receive the sample and a reference sensor component.

The reference sensor component can comprise a reference conduit comprising a reference conduit proximal end defining a reference conduit first opening, a reference conduit distal end defining a reference conduit second opening, and a reference conduit cavity in between the reference conduit proximal end and the reference conduit distal end.

The reference conduit cavity can be at least partially filled with a reference buffer solution. A segment of the reference conduit can extend into the sample chamber. A reference electrode can extend partially into the reference conduit cavity filled with the reference buffer solution.

An ion exchange membrane can be coupled to the reference conduit distal end and configured to obstruct the reference conduit second opening. The ion exchange membrane can be configured to prevent the sample from intermixing with the reference buffer solution but allow ions to transverse the ion exchange membrane.

The sensor apparatus can further comprise an active sensor component. The active sensor component can comprise an active electrode housing extending into the sample chamber and an active electrode housed partially within the active electrode housing.

The active electrode can comprise a sample contact surface. The active electrode can be disposed at a distal end of the active electrode housing and the active electrode housing can be configured to expose the sample contact surface such that the sample contact surface is in fluid communication with the sample.

A conductive contact layer can be coupled to the active electrode and positioned proximal to the active electrode within the active electrode housing. The conductive contact layer and the reference electrode can be electrically coupled by conductive connections to a voltmeter and wherein the pH of the sample is measured based on a potential difference between the active electrode and the reference electrode.

The reference conduit can comprise conduit walls. The conduit walls can taper from a reference conduit proximal end to a reference conduit distal end such that a first opening area of the reference conduit first opening is larger than a second opening area of the reference conduit second opening. The reference conduit cavity can be filled with about 100 µL to about 500 µL of reference buffer solution.

The reference electrode can comprise a reference electrode tip. The reference electrode tip can be positioned proximal to the ion exchange membrane when the reference electrode is partially extended into the reference conduit cavity such that a volume of reference buffer solution separates the reference electrode tip from the ion exchange membrane.

In some embodiments, the ion exchange membrane can be a perfluoro-sulfonated ionomer membrane. For example, the perfluoro-sulfonated ionomer membrane can be a Nafion® membrane. The ion exchange membrane can have a thickness of about 25 µm to about 180 µm.

The reference electrode can be made in part of one or more metals. For example, the reference electrode is made in part of platinum, stainless steel, or a combination thereof.

The active electrode can be made in part of a metal oxide. For example, the active electrode can be made in part of silicon dioxide, aluminum oxide, titanium dioxide, tantalum pentoxide, hafnium dioxide, iridium dioxide, ruthenium dioxide, zirconium dioxide, or a combination thereof.

The conductive contact layer can be made in part of one or more metals. In some embodiments, the conductive contact layer can be made in part of aluminum, copper, platinum, or a combination thereof.

The reference buffer solution can comprise potassium hexacyanoferrate(III), potassium hexacyanoferrate(II), potassium dihydrogen phosphate, disodium hydrogen phosphate, or a combination thereof. In other embodiments, the reference buffer solution can comprise potassium chloride.

The sensor apparatus can further comprise an aeration conduit. A segment of the aeration conduit extends into the sample chamber, and wherein the aeration conduit is configured to aerate the sample within the sample container.

The reference sensor component can be removably coupled to the sample container such that the reference sensor component is detachable from the sample container.

Disclosed herein is another embodiment of a sensor apparatus for measuring an oxidation-reduction potential (ORP) of a sample. The sensor apparatus comprising a sample container comprising a sample chamber configured to receive the sample and a reference sensor component.

The reference sensor component can comprise a reference conduit comprising a reference conduit proximal end defining a reference conduit first opening, a reference conduit distal end defining a reference conduit second opening, and a reference conduit cavity in between the reference conduit proximal end and the reference conduit distal end. The reference conduit cavity can be at least partially filled with a reference buffer solution. A segment of the reference conduit can extend into the sample chamber. The sensor apparatus can further comprise a reference electrode extending partially into the reference conduit cavity filled with the reference buffer solution.

An ion exchange membrane can be coupled to the reference conduit distal end and configured to obstruct the reference conduit second opening. The ion exchange membrane can be configured to prevent the sample from intermixing with the reference buffer solution but allow ions to transverse the ion exchange membrane.

Moreover, the sensor apparatus can comprise an active sensor component. The active sensor component can comprise an active electrode housing extending into the sample chamber and an active electrode housed partially within the active electrode housing.

The active electrode can comprise a sample contact surface. The active electrode can be disposed at a distal end of the active electrode housing and the active electrode housing is configured to expose the sample contact surface such that the sample contact surface is in fluid communication with the sample.

The active electrode and the reference electrode can be electrically coupled by conductive connections to a voltmeter. The ORP of the sample can be measured based on a potential difference between the active electrode and the reference electrode.

The reference conduit can comprise conduit walls. In some embodiments, the conduit walls can taper from a reference conduit proximal end to a reference conduit distal end such that a first opening area of the reference conduit first opening is larger than a second opening area of the reference conduit second opening. The reference conduit cavity can be filled with about 100 µL to about 500 µL of reference buffer solution.

The reference electrode can comprise a reference electrode tip. The reference electrode tip can be positioned proximal to the ion exchange membrane when the reference electrode is partially extended into the reference conduit cavity such that a volume of reference buffer solution separates the reference electrode tip from the ion exchange membrane.

The reference electrode can be made in part of one or more metals. For example, the reference electrode can be made in part of platinum, stainless steel, or a combination thereof.

The active electrode can be made in part of one or more metals, one or more metal oxides, or a combination thereof. For example, the active electrode can be made in part of platinum, gold, silicon dioxide, aluminum oxide, titanium dioxide, tantalum pentoxide, hafnium dioxide, iridium dioxide, ruthenium dioxide, zirconium dioxide, or a combination thereof.

In some embodiments, the reference buffer solution can comprise potassium hexacyanoferrate(III), potassium hexacyanoferrate(II), potassium dihydrogen phosphate, disodium hydrogen phosphate, or a combination thereof. In other embodiments, the reference buffer solution can comprise potassium chloride.

As previously discussed, an ion exchange membrane can be coupled to the reference conduit distal end and configured to obstruct the reference conduit second opening. In some embodiments, the ion exchange membrane can be a perfluoro-sulfonated ionomer membrane. For example, the perfluoro-sulfonated ionomer membrane can be a Nafion® membrane. The ion exchange membrane can have a thickness of about 25 µm to about 180 µm.

The sensor apparatus can further comprise an aeration conduit. A segment of the aeration conduit can extend into the sample chamber. The aeration conduit can be configured to aerate the sample within the sample container.

The reference sensor component can be removably coupled to the sample container such that the reference sensor component is detachable from the sample container.

DETAILED DESCRIPTION

Variations of the devices, systems, and methods described herein are best understood from the detailed description when read in conjunction with the accompanying drawings. It is emphasized that, according to common practice, the various features of the drawings may not be to scale. The dimensions of certain features have been expanded or reduced for clarity and not all features may be visible or labeled in every drawing. The drawings are taken for illustrative purposes only and are not intended to define or limit the scope of the claims to that which is shown.

Figure 1A:
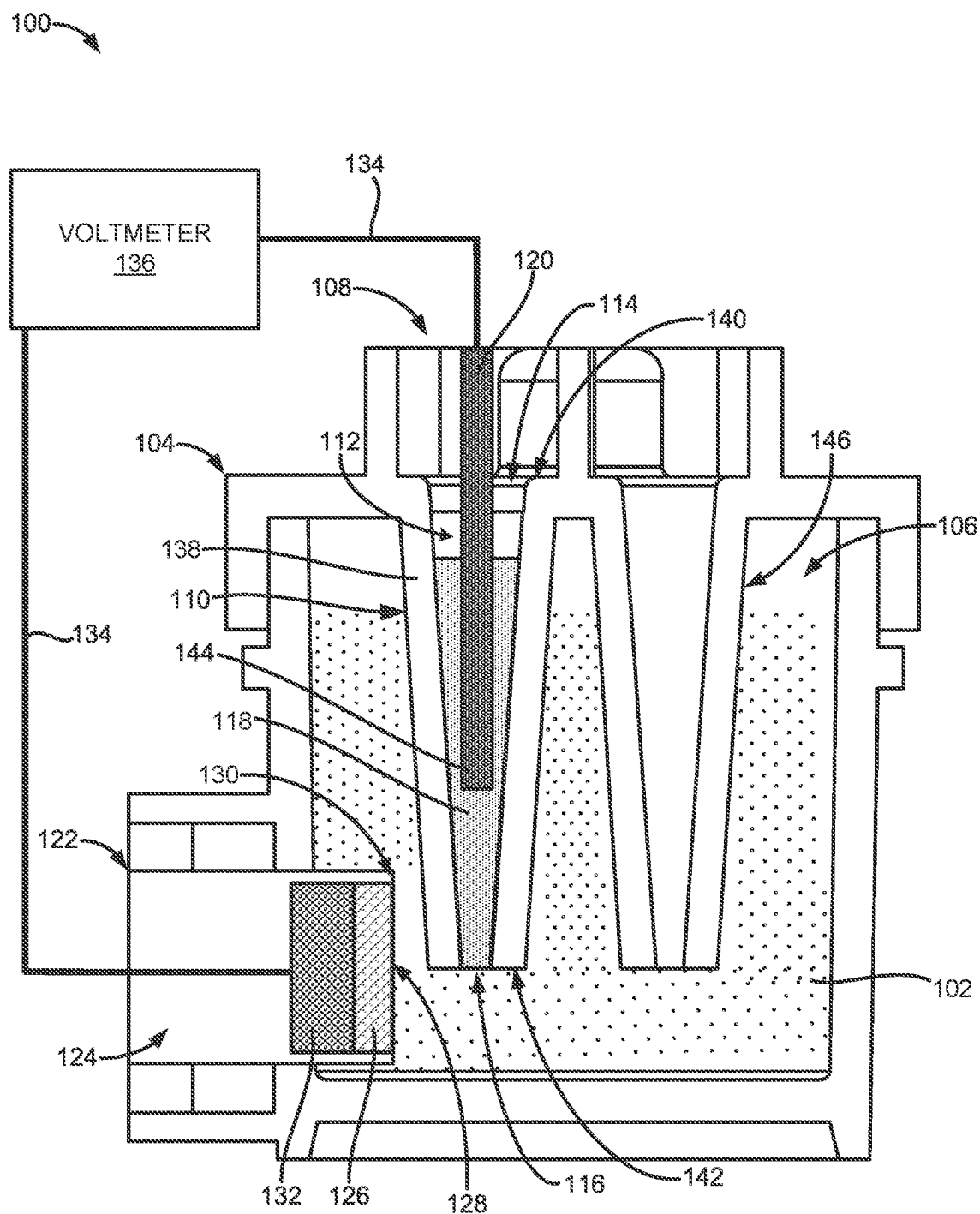
FIG. 1A illustrates an embodiment of a sensor apparatus for measuring a pH of a sample.

FIG. 1A illustrates an embodiment of a sensor apparatus 100 for measuring a pH of a sample 102. FIG. 1A illustrates a side cross-sectional view of the sensor apparatus 100.

The sensor apparatus 100 can comprise a sample container 104 having a sample chamber 106 configured to receive the sample 102. The sample 102 can comprise at least one of a sample obtained from a patient or subject, a biological sample, an environmental sample, and a food sample. The sample 102 obtained from the patient or subject can comprise at least one of a bodily fluid of the patient or subject and a swab obtained from the patient or subject.

In some embodiments, the patient or subject can be a human patient or subject. In other embodiments, the patient or subject can be a non-human animal patient or subject.

In some embodiments, the bodily fluid can comprise blood, urine, serum, plasma, saliva, sputum, semen, breast milk, joint fluid, spinal fluid such as cerebrospinal fluid, wound material, mucus, fluid accompanying stool, vaginal secretions, synovial fluid, pleural fluid, peritoneal fluid, pericardial fluid, amniotic fluid, or a combination thereof.

In these and other embodiments, the swab obtained from the patient or subject can comprise a wound swab, a rectal swab, a vaginal swab, re-suspended instances of the aforementioned swabs, or a combination thereof.

In all such embodiments, the sample 102 can comprise a number of microorganisms or infectious agents. The apparatus, systems, and methods disclosed herein can be used to assay the sample 102 for microbial growth or lack thereof as part of a microbial quantification procedure or an antibiotic susceptibility testing (AST) procedure.

In certain embodiments, the sample 102 can comprise or refer to a bacterial culture derived from at least one of a sample obtained from a patient or subject, a biological sample, an environmental sample, and a food sample. For example, the sample 102 can comprise or refer to a bacterial culture or a re-suspended bacterial culture derived from a bodily fluid or swab obtained from a patient or subject. As a more specific example, the sample 102 can comprise a bacterial culture or a re-suspended bacterial culture derived from a bodily fluid or swab obtained from a patient or subject that has tested positive for microorganism growth.

More specifically, the sample 102 can comprise a bacterial culture derived from blood obtained from a patient or subject that has tested positive for microorganism growth. In some embodiments, the sample 102 can be or refer to a positive blood culture. For purposes of this disclosure, a positive blood culture can be a bacterial culture derived from blood drawn from a patient or subject that has tested positive for bacterial growth. For example, a patient can show symptoms of sepsis (e.g., high fever, chills, etc.) and blood (e.g., 5 mL to 10 mL) can be drawn from the patient and transferred into a commercial blood culturing container or vessel that contain bacterial growth media (e.g., 30 mL to 40 mL of growth media). The blood culturing container or vessel can then be incubated at 35° C.±2° C. to allow the bacteria to proliferate. If the patient's blood is contaminated with bacteria, the bacteria will replicate within the container or vessel. A blood culturing system or apparatus can then be used to monitor for bacterial growth (such as by monitoring bacterial $CO_2$ production within the container or vessel) and the system or apparatus can determine the sample as testing "positive" for bacterial growth when a critical $CO_2$ threshold has been met. Depending on the pathogen type and growth rate, the blood culture can turn positive between 7 hours and 3 days. Such a "positive blood culture" can then be used for further downstream testing such as using any of the apparatus, systems, and methods disclosed herein.

In additional embodiments, the sample 102 can comprise an environmental sample obtained from a stream, river, lake, ocean, contamination site, quarantine zone, an emergency area, or a combination thereof. In other embodiments, the sample 102 can comprise a food sample obtained from a food preparation facility, a dining establishment, a waste facility, or a combination thereof.

In some embodiments, an aqueous growth media can be added to the sample 102 prior to being introduced into the sample container 104. In other embodiments, the aqueous growth media can be added to the sample 102 once the sample 102 has been injected, delivered, or otherwise introduced into the sample container 104.

In one embodiment, the aqueous growth media can be a glucose supplemented Mueller Hinton broth (MHG). In other embodiments, the aqueous growth media can be a solution containing bacto-tryptone, tryptic soy digest, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose or other carbohydrates, or a combination thereof.

The microorganisms or infectious agents that can be assayed using the apparatus, methods, and systems disclosed herein can be any metabolizing single- or multi-cellular organism including bacteria and fungi. In certain embodiments, the microorganisms or infectious agents can be bacteria selected from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the microorganisms or infectious agents can be one or more fungi selected from the genera *Candida* or *Cryptococcus* or mold.

Other specific bacteria that can be assayed using the methods and systems disclosed herein can comprise *Staphylococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans, Candida glabrata*, and *Candida tropicalis*.

Other more specific bacteria that can be assayed can comprise *Acinetobacter baumannii, Actinobacillus* spp., Actinomycetes, *Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae, Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* spp. (including but not limited to *Brucella abortus, Brucella canis, Brucella* melintensis and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp., *Coxiella burnetii, Corynebacterium* spp. (including but not limited to, *Corynebacterium diphtheriae, Corynebacterium* jeikeum and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*), *Enterococcus* spp. (including but not limited to *Enterococcusfaecalis* and *Enterococcus faecium*), *Ehrlichia* spp. (including but not limited to *Ehrlichia* chafeensia and *Ehrlichia canis*), Erysipelothrix rhusiopathiae, *Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus, Helicobacter* spp. (including but not limited to *Helicobacter pylori, Helicobacter cinaedi* and *Helicobacter fennelliae*), Kingella *kingii, Klebsiella* spp. (including but not limited to *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides, Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa, Propionibacterium acnes, Rhodococcus equi, Rickettsia* spp. (including but not limited to *Rickettsia rickettsii, Rickettsia akari* and *Rickettsia prowazekii*, Orientia tsutsugamushi (formerly: *Rickettsia* tsutsugamushi) and *Rickettsia typhi*), *Rhodococcus* spp., *Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes, Group A Streptococci, Streptococcus pyogenes, Group B Streptococci, Streptococcus agalactiae, Group C Streptococci, Streptococcus anginosus, Streptococcus equismilis, Group D Streptococci, Streptococcus bovis, Group F Streptococci, Streptococcus anginosus, and Group G Streptococci), Spirillum minus, Streptobacillus moniliformi, Treponema spp. (including but not limited to Treponema carateum, Treponema petenue, Treponema pallidum and Treponema endemicum, Tropheryma whippelii, Ureaplasma urealyticum, Veillonella spp., Vibrio spp. (including but not limited to Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela and Vibrio furnisii), Yersinia spp. (including but not limited to Yersinia enterocolitica, Yersinia pestis, and Yersinia pseudotuberculosis) and Xanthomonas maltophilia among others.

Furthermore, other microorganisms or infectious agents that can be assayed using the methods and systems disclosed herein can comprise fungi or mold including, but not limited to, Candida spp. (including but not limited to Candida albicans, Candida glabrata, Candida tropicalis, Candida parapsilosis, and Candida krusei), Aspergillus spp. (including but not limited to Aspergillus fumigatous, Aspergillus flavus, Aspergillus clavatus), Cryptoccocous spp. (including but not limited to Cryptococcus neoformans, Cryptococcus gattii, Cryptococcus laurentii, and Cryptococcus albidus), Fusarium spp. (including but not limited to Fusarium oxysporum, Fusarium solani, Fusarium verticillioides, and Fusarium proliferatum), Rhizopus oryzae, Penicillium marneffei, Coccidiodes immitis, and Blastomyces dermatitidis.

The sample container 104 can be made in part of an inert or non-conductive material. In some embodiments, the sample container 104 can comprise or be made in part of a polymeric material, a ceramic material or glass, or a combination thereof. As a more specific example, the sample container 104 can comprise or be made in part of polyvinyl chloride (PVC), poly(methyl methacrylate) (PMMA), polydimethylsiloxane (PDMS), or a combination thereof.

The sensor apparatus 100 can also comprise a reference sensor component 108 and an active sensor component 122. The reference sensor component 108 can further comprise a reference conduit 110 comprising a reference conduit cavity 112, a reference conduit first opening 114, and a reference conduit second opening 116.

The reference conduit 110 can comprise conduit walls 138 and the conduit walls 138 can taper from a reference conduit proximal end 140 to a reference conduit distal end 142. In one embodiment, the reference conduit 110 can be substantially shaped as a conic or frustoconic having a reference conduit cavity 112 also substantially shaped as a conic or frustoconic. In other embodiments, the reference conduit 110 can be substantially shaped as an elongate pyramid having a polygonal-shaped base. For example, the reference conduit 110 can be substantially shaped as an elongate triangular pyramid, square pyramid, or a pentagonal pyramid. In additional embodiments, the reference conduit 110 can be substantially shaped as a cylinder having a substantially cylindrical-shaped reference conduit cavity 112. In these embodiments, the reference conduit 110 can also have a tapered reference conduit distal end 142.

The reference conduit cavity 112 can be at least partially filled with a reference buffer gel 118. The reference conduit 110 can extend into the sample chamber 106 such that the reference conduit second opening 116 is configured to allow the sample 102 to be in fluid contact with the reference buffer gel 118 within the reference conduit cavity 112. For example, the reference conduit second opening 116 can allow the sample 102 to be in liquid-solid contact with the reference buffer gel 118. In this manner, a salt bridge can be formed with the liquid-solid interface acting as the interface of the salt bridge.

In one embodiment, the reference buffer gel 118 can be an agar gel formed from agar powder mixed with a reference buffer solution. In other embodiments, the reference buffer gel 118 can be a gel formed from other types of polysaccharides mixed with a reference buffer solution. As a more specific example, the agar powder used can be a commercially available agar powder such as agar powder provided by Sigma-Aldrich, Inc. (e.g., Sigma-Aldrich™ Agar Powder 05040) or Thermo Fisher Scientific Inc. (e.g., Fisher Scientific™ Agar Powder, Catalog No. S14153).

The reference buffer solution can be an aqueous redox buffer solution. In one embodiment, the reference buffer solution can be an aqueous redox buffer solution comprising deionized water, potassium hexacyanoferrate, dihydrogen phosphate, disodium hydrogen phosphate, or a combination thereof. For example, the reference buffer solution can be an aqueous redox buffer solution comprising deionized water (e.g., about 95%-99%), potassium hexacyanoferrate(III) (e.g., about 0.1% to 0.9%), potassium hexacyanoferrate(II) (e.g., about 0.1% to 0.9%), potassium dihydrogen phosphate (e.g., less than about 0.5%), and disodium hydrogen phosphate (less than about 0.5%). As a more specific example, the reference buffer solution can be a 220 mV/pH 7 redox buffer solution (Product Code 51350060) provided by Mettler-Toledo AG.

In other embodiments, the reference buffer solution can be an aqueous redox buffer solution comprising 3M KCl. As a more specific example, the reference buffer solution can be 3M KCl redox buffer solution (Material No. 63056165) provided by Mettler-Toledo AG.

In one embodiment, the reference buffer gel 118 can comprise agar powder at a concentration of about 1% (w/v %, g/mL). In another embodiment, the reference buffer gel 118 can comprise agar powder at a concentration of about 5% (w/v %, g/mL). In some embodiments, the reference buffer gel 118 can comprise agar powder at a concentration of between about 1% (w/v %, g/mL) and 5% (w/v %, g/mL). In other embodiments, the reference buffer gel 118 can comprise agar powder at a concentration of between about 5% (w/v %, g/mL) and 10% (w/v %, g/mL).

The reference buffer gel 118 can be made by heating the aqueous reference buffer solution above the boiling point of the aqueous reference buffer solution and stirring the agar powder into the heated aqueous reference buffer solution. Once the agar powder is completely dissolved in the heated aqueous reference buffer solution, the hot gel slurry can be poured into the reference conduit cavity 112 and allowed to cool to room temperature. The reference buffer gel 118 can solidify when the hot gel cools to room temperature within the reference conduit cavity 112.

In one embodiment, the reference conduit cavity 112 can be filled with about 100 µL of reference buffer gel 118. In another embodiment, the reference conduit cavity 112 can be filled with about 500 µL of reference buffer gel 118. In other embodiments, the reference conduit cavity 112 can be filled with about 100 µL to about 500 µL of reference buffer gel 118. In further embodiments, the reference conduit cavity 112 can be filled with about 500 µL to about 1 mL of reference buffer gel 118. The amount of reference buffer gel 118 can depend on the volume of the reference conduit cavity 112, the size of the reference conduit 110, the size of the sample container 104, or a combination thereof.

The reference sensor component 108 can also comprise a reference electrode 120 extending into the reference conduit cavity 112 filled with the reference buffer gel 118. The reference electrode 120 can extend partially into the reference conduit cavity 112 filled with the reference buffer gel 118.

As a more specific example, the reference electrode 120 can comprise a reference electrode tip 144. The reference electrode tip 144 can be positioned proximal to the reference conduit second opening 116 when the reference electrode 120 is partially extended into the reference conduit cavity 112 filled with the reference buffer gel 118. More specifically, a volume of reference buffer gel 118 can separate the reference electrode tip 144 from the reference conduit second opening 116. The position of the reference electrode 120 within the reference conduit cavity 112 will be discussed in more detail in the following sections.

The reference electrode 120 can be made in part of one or more metals. In one embodiment, the reference electrode 120 can be made in part of platinum (Pt), stainless steel, or a combination thereof. In other embodiments, the reference electrode 120 can be made in part of another type of conductive metal. For example, the reference electrode 120 can be a metallic pin, wire, or rod inserted into the reference buffer gel 118 such that a segment of the reference electrode 120 (e.g., the reference electrode tip 144 and the segment of the reference electrode 120 in proximity to the reference electrode tip 144) pierces the reference buffer gel 118 and resides within the reference buffer gel 118.

One unexpected discovery made by the applications is that the reference buffer gel 118 slows diffusion across the solid-liquid interface created by the reference buffer gel 118 and the sample 102 and lengthens the amount of time that such a reference sensor component 108 can be used as a viable reference cell for pH measurements.

The sensor apparatus 100 can also comprise an active sensor component 122 comprising an active electrode housing 124 extending into the sample chamber 106 configured to receive the sample 102. The active sensor component 122 can also comprise an active electrode 126 at least partially housed or surrounded by the active electrode housing 124.

The active electrode housing 124 can be made of an inert or non-conductive material. The active electrode housing 124 can comprise, a polymeric material such as polyvinyl chloride (PVC), poly(methyl methacrylate) (PMMA), polydimethylsiloxane (PDMS), a ceramic, silicon dioxide ($SiO_2$) or types of glass, or a combination thereof.

The active electrode 126 can comprise a sample contact surface 128. The active electrode 126 can be disposed at an active component distal end 130. The active electrode housing 124 can be configured to expose the sample contact surface 128 such that the sample contact surface 128 is in fluid communication with the sample 102.

In some embodiments, the active electrode 126 can be made in part of a metal oxide. For example, the active electrode 126 can be made in part of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

The active sensor component 122 can also comprise a conductive contact layer 132 coupled to the active electrode 126 and positioned proximal to the active electrode 126. The conductive contact layer 132 can also be housed within or encased by the active electrode housing 124.

The conductive contact layer 132 can be made in part of one or more metals. In some embodiments, the conductive contact layer 132 can be made in part of aluminum (Al), copper (Cu), platinum (Pt), or a combination thereof. The conductive contact layer 132 and the reference electrode 120 can be electrically coupled by conductive connections 134 or conductive traces to a voltmeter 136. The conductive connections 134 can be made in part of a conductive material. In one embodiment, the conductive connections 134 can be copper traces. For example, the conductive connections 134 can be electro-deposited copper, rolled annealed copper, high-ductility electro-deposited copper, or a combination thereof. In other embodiments, the conductive connections 134 can be made in part of silver or nickel.

In some embodiments, the voltmeter 136 can be a high-impedance voltmeter. The conductive connections 134 can electrically couple the active electrode 126 (via the conductive contact layer 132) and the reference electrode 120 to the voltmeter 136. The pH of the sample 102 can be measured based on a potential difference between the active electrode 126 and the reference electrode 120.

The sensor apparatus 100 can also comprise an aeration conduit 146. A segment of the aeration conduit 146 can extend into the sample chamber 106 such that a lumen or cavity within the aeration conduit 146 is in fluid communication with the sample chamber 106. The aeration conduit 146 can be configured to aerate the sample 102 received within the sample container 104. Aerating the sample 102 can enhance a growth rate of microorganisms within the sample 102 by increasing the supply of oxygen to such microorganisms. Moreover, aeration can also enable detachment of the microorganisms from the interior walls of the sample container 104 so as to inhibit biofilm formation.

Figure 1B:
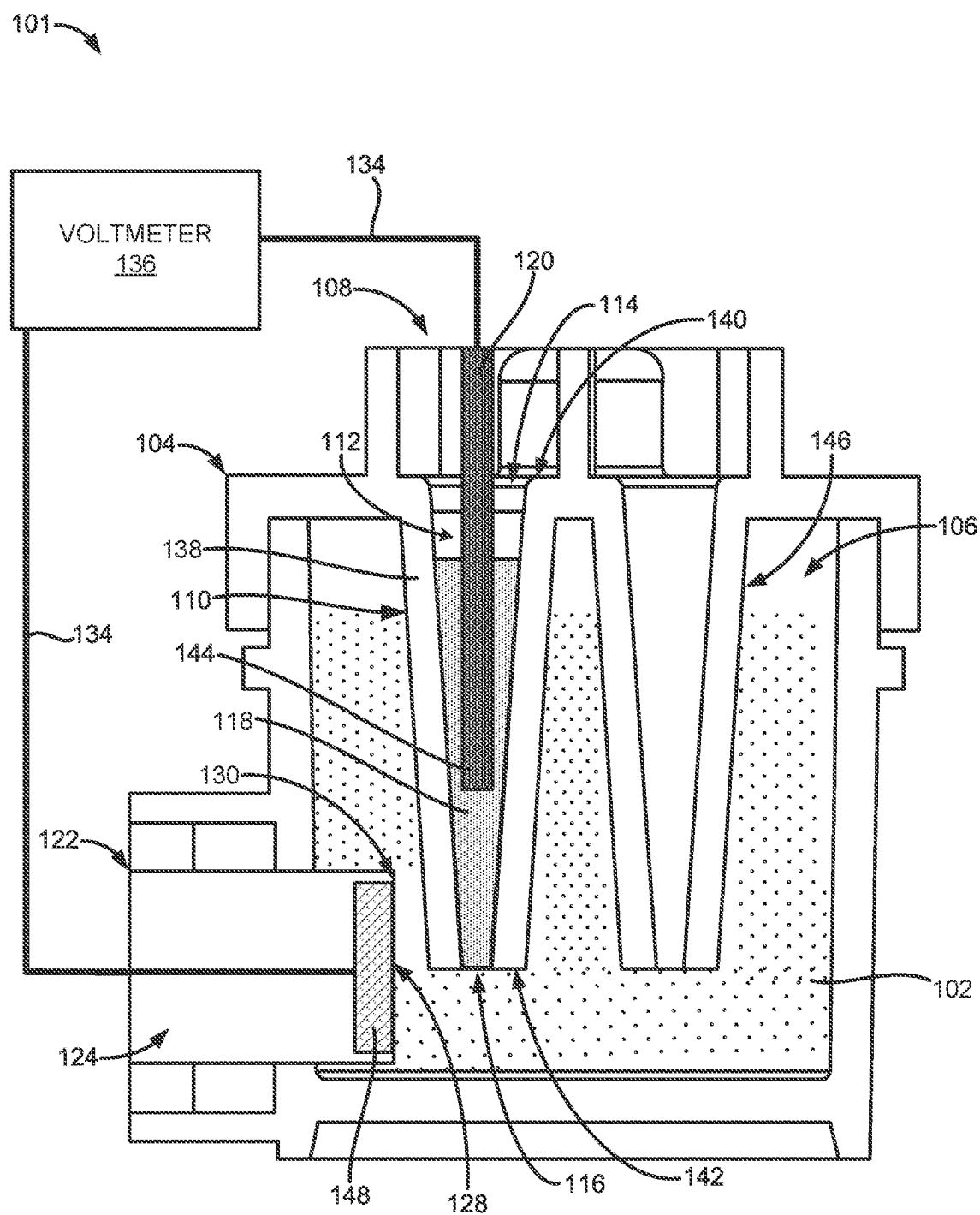
FIG. 1B illustrates an embodiment of a sensor apparatus for measuring an ORP of a sample.

FIG. 1B illustrates an embodiment of a sensor apparatus 101 for measuring an oxidation-reduction potential (ORP) of a sample 102. FIG. 1B illustrates a side cross-sectional view of the sensor apparatus 101.

The sensor apparatus 101 can comprise a sample container 104 having a sample chamber 106 configured to receive the sample 102. The sample 102 can be the same sample 102 discussed with respect to the sensor apparatus 100 (as shown in FIG. 1A). The sample 102 can comprise a number of microorganisms or infectious agents. The apparatus, systems, and methods disclosed herein can be used to assay the sample 102 for microbial growth or lack thereof as part of a microbial quantification procedure or an antibiotic susceptibility testing (AST) procedure.

In some embodiments, an aqueous growth media can be added to the sample 102 prior to being introduced into the sample container 104. In other embodiments, the aqueous growth media can be added to the sample 102 once the sample 102 has been injected, delivered, or otherwise introduced into the sample container 104.

In one embodiment, the aqueous growth media can be a glucose supplemented Mueller Hinton broth (MHG). In other embodiments, the aqueous growth media can be a solution containing bacto-tryptone, tryptic soy digest, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose or other carbohydrates, or a combination thereof.

The sample container 104 can be made in part of an inert or non-conductive material. In some embodiments, the sample container 104 can comprise or be made in part of a polymeric material, a ceramic material or glass, or a combination thereof. As a more specific example, the sample container 104 can comprise or be made in part of polyvinyl chloride (PVC), poly(methyl methacrylate) (PMMA), polydimethylsiloxane (PDMS), or a combination thereof.

The sensor apparatus 101 can also comprise a reference sensor component 108 and an active sensor component 122. The reference sensor component 108 can further comprise a reference conduit 110 comprising a reference conduit cavity 112, a reference conduit first opening 114, and a reference conduit second opening 116.

The reference conduit 110 can comprise conduit walls 138. The conduit walls 138 can taper from a reference conduit proximal end 140 to a reference conduit distal end 142. In one embodiment, the reference conduit 110 can be substantially shaped as a conic or frustoconic having a reference conduit cavity 112 also substantially shaped as a conic or frustoconic. In other embodiments, the reference conduit 110 can be substantially shaped as an elongate pyramid having a polygonal-shaped base. For example, the reference conduit 110 can be substantially shaped as an elongate triangular pyramid, square pyramid, or a pentagonal pyramid. In additional embodiments, the reference conduit 110 can be substantially shaped as a cylinder having a substantially cylindrical-shaped reference conduit cavity 112. In these embodiments, the reference conduit 110 can also have a tapered reference conduit distal end 142.

The reference conduit cavity 112 can be at least partially filled with a reference buffer gel 118. The reference conduit 110 can extend into the sample chamber 106 such that the reference conduit second opening 116 is configured to allow the sample 102 to be in fluid contact with the reference buffer gel 118 within the reference conduit cavity 112. For example, the reference conduit second opening 116 can allow the sample 102 to be in liquid-solid contact with the reference buffer gel 118. In this manner, a salt bridge can be formed with the liquid-solid interface acting as the interface of the salt bridge.

In one embodiment, the reference buffer gel 118 can be an agar gel formed from agar powder mixed with a reference buffer solution. In other embodiments, the reference buffer gel 118 can be a gel formed from other types of polysaccharides mixed with a reference buffer solution. As a more specific example, the agar powder used can be a commercially available agar powder such as agar powder provided by Sigma-Aldrich, Inc. (e.g., Sigma-Aldrich™ Agar Powder 05040) or Thermo Fisher Scientific Inc. (e.g., Fisher Scientific™ Agar Powder, Catalog No. S14153).

The reference buffer solution can be an aqueous redox buffer solution. In one embodiment, the reference buffer solution can be an aqueous redox buffer solution comprising deionized water, potassium hexacyanoferrate, dihydrogen phosphate, disodium hydrogen phosphate, or a combination thereof. For example, the reference buffer solution can be an aqueous redox buffer solution comprising deionized water (e.g., about 95%-99%), potassium hexacyanoferrate(III) (e.g., about 0.1% to 0.9%), potassium hexacyanoferrate(II) (e.g., about 0.1% to 0.9%), potassium dihydrogen phosphate (e.g., less than about 0.5%), and disodium hydrogen phosphate (less than about 0.5%). As a more specific example, the reference buffer solution can be a 220 mV/pH 7 redox buffer solution (Product Code 51350060) provided by Mettler-Toledo AG.

In other embodiments, the reference buffer solution can be an aqueous redox buffer solution comprising 3M KCl. As a more specific example, the reference buffer solution can be 3M KCl redox buffer solution (Material No. 63056165) provided by Mettler-Toledo AG.

In one embodiment, the reference buffer gel 118 can comprise agar powder at a concentration of about 1% (w/v %, g/mL). In another embodiment, the reference buffer gel 118 can comprise agar powder at a concentration of about 5% (w/v %, g/mL). In some embodiments, the reference buffer gel 118 can comprise agar powder at a concentration of between about 1% (w/v %, g/mL) and 5% (w/v %, g/mL). In other embodiments, the reference buffer gel 118 can comprise agar powder at a concentration of between about 5% (w/v %, g/mL) and 10% (w/v %, g/mL).

The reference buffer gel 118 can be made by heating the aqueous reference buffer solution above the boiling point of the aqueous reference buffer solution and stirring the agar powder into the heated aqueous reference buffer solution. Once the agar powder is completely dissolved in the heated aqueous reference buffer solution, the hot gel slurry can be poured into the reference conduit cavity 112 and allowed to cool to room temperature. The reference buffer gel 118 can solidify when the hot gel cools to room temperature within the reference conduit cavity 112.

In one embodiment, the reference conduit cavity 112 can be filled with about 100 µL of reference buffer gel 118. In another embodiment, the reference conduit cavity 112 can be filled with about 500 µL of reference buffer gel 118. In other embodiments, the reference conduit cavity 112 can be filled with about 100 µL to about 500 µL of reference buffer gel 118. In further embodiments, the reference conduit cavity 112 can be filled with about 500 µL to about 1 mL of reference buffer gel 118. The amount of reference buffer gel 118 can depend on the volume of the reference conduit cavity 112, the size of the reference conduit 110, the size of the sample container 104, or a combination thereof.

The reference sensor component 108 can also comprise a reference electrode 120 extending into the reference conduit cavity 112 filled with the reference buffer gel 118. The reference electrode 120 can extend partially into the reference conduit cavity 112 filled with the reference buffer gel 118.

As a more specific example, the reference electrode 120 can comprise a reference electrode tip 144. The reference electrode tip 144 can be positioned proximal to the reference conduit second opening 116 when the reference electrode 120 is partially extended into the reference conduit cavity 112 filled with the reference buffer gel 118. More specifically, a volume of reference buffer gel 118 can separate the reference electrode tip 144 from the reference conduit second opening 116. The position of the reference electrode 120 within the reference conduit cavity 112 will be discussed in more detail in the following sections.

The reference electrode 120 can be made in part of one or more metals. In one embodiment, the reference electrode 120 can be made in part of platinum (Pt), stainless steel, or a combination thereof. In other embodiments, the reference electrode 120 can be made in part of another type of conductive metal. For example, the reference electrode 120 can be a metallic pin, wire, or rod inserted into the reference buffer gel 118 such that a segment of the reference electrode 120 (e.g., the reference electrode tip 144 and the segment of the reference electrode 120 in proximity to the reference electrode tip 144) pierces the reference buffer gel 118 and resides within the reference buffer gel 118.

One unexpected discovery made by the applications is that the reference buffer gel 118 slows diffusion across the solid-liquid interface created by the reference buffer gel 118 and the sample 102 and lengthens the amount of time that such a reference sensor component 108 can be used as a viable reference cell for ORP measurements.

The sensor apparatus 101 can also comprise an active sensor component 122 comprising an active electrode housing 124 extending into the sample chamber 106 configured to receive the sample 102. The active sensor component 122 can also comprise an active electrode 148 at least partially housed or surrounded by the active electrode housing 124.

The active electrode housing 124 can be made of an inert or non-conductive material. The active electrode housing 124 can comprise, a polymeric material such as polyvinyl chloride (PVC), poly(methyl methacrylate) (PMMA), polydimethylsiloxane (PDMS), a ceramic, silicon dioxide ($SiO_2$) or types of glass, or a combination thereof.

The active electrode 148 can comprise a sample contact surface 128. The active electrode 148 can be disposed at an active component distal end 130. The active electrode housing 124 can be configured to expose the sample contact surface 128 such that the sample contact surface 128 is in fluid communication with the sample 102.

In some embodiments, the active electrode 148 can be made in part of one or more metals, one or more metal oxides, or a combination thereof. For example, the active electrode 148 can be made in part of platinum (Pt), gold (Au), a redox sensitive metal oxide, or a combination thereof. In some embodiments, the redox sensitive metal oxide can comprise silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

The active electrode 148 and the reference electrode 120 can be electrically coupled by conductive connections 134 or conductive traces to a voltmeter 136. The conductive connections 134 can be made in part of a conductive material. In one embodiment, the conductive connections 134 can be copper traces. For example, the conductive connections 134 can be electro-deposited copper, rolled annealed copper, high-ductility electro-deposited copper, or a combination thereof. In other embodiments, the conductive connections 134 can be made in part of silver or nickel.

In some embodiments, the voltmeter 136 can be a high-impedance voltmeter. The ORP of the sample 102 can be measured based on a potential difference between the active electrode 148 and the reference electrode 120.

The sensor apparatus 101 can also comprise an aeration conduit 146. A segment of the aeration conduit 146 can extend into the sample chamber 106 such that a lumen or cavity within the aeration conduit 146 is in fluid communication with the sample chamber 106. The aeration conduit 146 can be configured to aerate the sample 102 received within the sample container 104. Aerating the sample 102 can enhance a growth rate of microorganisms within the sample 102 by increasing the supply of oxygen to such microorganisms. Moreover, aeration can also enable detachment of the microorganisms from the interior walls of the sample container 104 so as to inhibit biofilm formation.

Figure 1C:
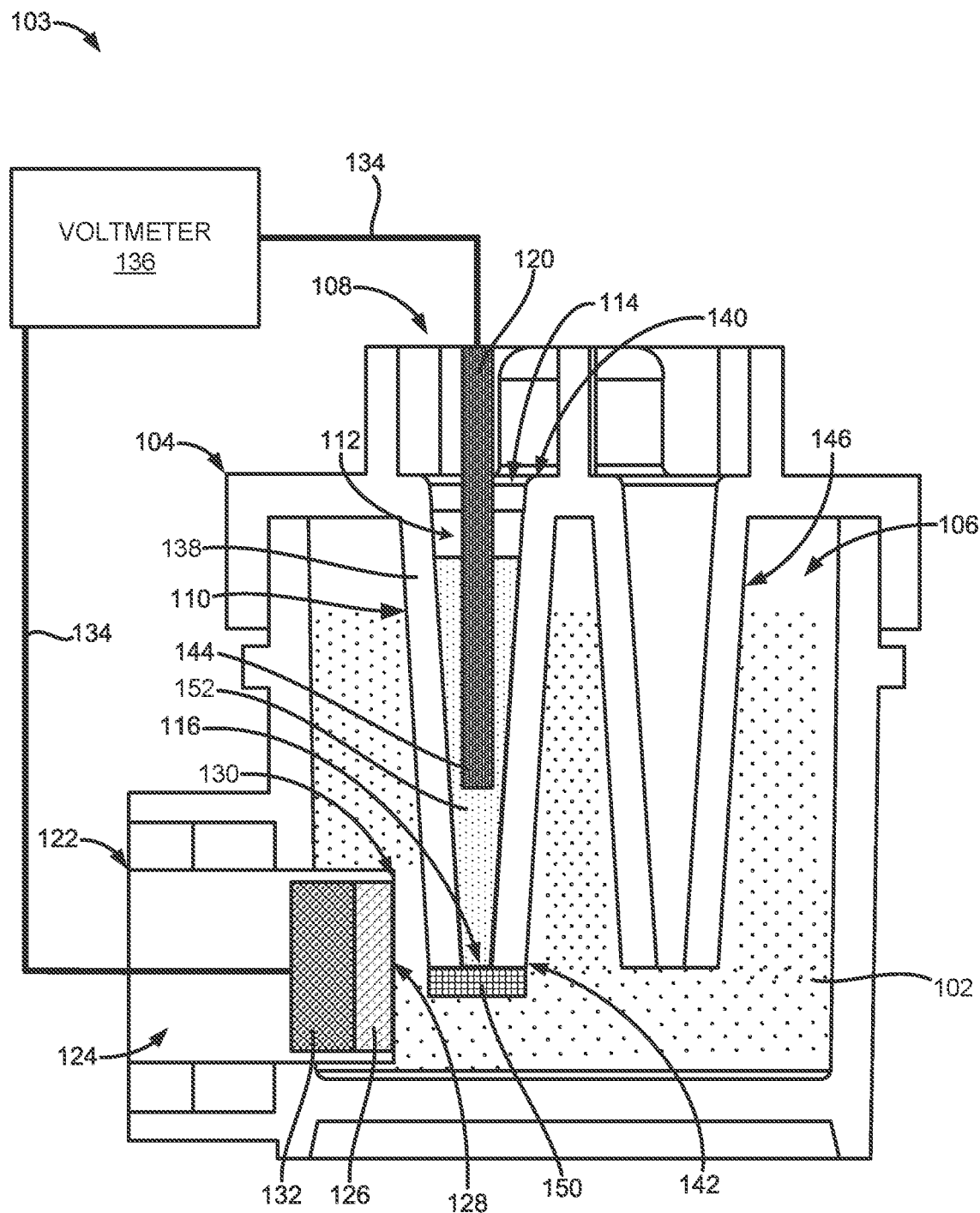
FIG. 1C illustrates another embodiment of a sensor apparatus for measuring a pH of a sample.

FIG. 1C illustrates another embodiment of a sensor apparatus 103 for measuring a pH of a sample 102. FIG. 1C illustrates a side cross-sectional view of the sensor apparatus 103.

The sensor apparatus 103 can comprise a sample container 104 having a sample chamber 106 configured to receive the sample 102. The sample 102 can be the same sample 102 discussed with respect to the sensor apparatus 100 (as shown in FIG. 1A) and the sensor apparatus 101 (as shown in FIG. 1B). The sample 102 can comprise a number of microorganisms or infectious agents. The apparatus, systems, and methods disclosed herein can be used to assay the sample 102 for microbial growth or lack thereof as part of a microbial quantification procedure or an antibiotic susceptibility testing (AST) procedure.

In some embodiments, an aqueous growth media can be added to the sample 102 prior to being introduced into the sample container 104. In other embodiments, the aqueous growth media can be added to the sample 102 once the sample 102 has been injected, delivered, or otherwise introduced into the sample container 104.

In one embodiment, the aqueous growth media can be a glucose supplemented Mueller Hinton broth (MHG). In other embodiments, the aqueous growth media can be a solution containing bacto-tryptone, tryptic soy digest, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose or other carbohydrates, or a combination thereof.

The sample container 104 can be made in part of an inert or non-conductive material. In some embodiments, the sample container 104 can comprise or be made in part of a polymeric material, a ceramic material or glass, or a combination thereof. As a more specific example, the sample container 104 can comprise or be made in part of polyvinyl chloride (PVC), poly(methyl methacrylate) (PMMA), polydimethylsiloxane (PDMS), or a combination thereof.

The sensor apparatus 103 can also comprise a reference sensor component 108 and an active sensor component 122. The reference sensor component 108 can further comprise a reference conduit 110 comprising a reference conduit proximal end 140 defining a reference conduit first opening 114, a reference conduit distal end 142 defining a reference conduit second opening 116, and a reference conduit cavity 112 in between the reference conduit proximal end 140 and the reference conduit distal end 142.

The reference conduit 110 can comprise conduit walls 138 and the conduit walls 138 can taper from a reference conduit proximal end 140 to a reference conduit distal end 142. In one embodiment, the reference conduit 110 can be substantially shaped as a conic or frustoconic having a reference conduit cavity 112 also substantially shaped as a conic or frustoconic. In other embodiments, the reference conduit 110 can be substantially shaped as an elongate pyramid having a polygonal-shaped base. For example, the reference conduit 110 can be substantially shaped as an elongate triangular pyramid, square pyramid, or a pentagonal pyramid. In additional embodiments, the reference conduit 110 can be substantially shaped as a cylinder having a substantially cylindrical-shaped reference conduit cavity 112. In these embodiments, the reference conduit 110 can also have a tapered reference conduit distal end 142.

The reference conduit 110 can extend into the sample chamber 106 such that at least a portion of the reference conduit 110 is immersed in the sample 102 when the sample chamber 106 is filled with the sample 102. For example, the reference conduit distal end 142 can be immersed in the sample 102 within the sample chamber 106.

The reference sensor component 108 can comprise an ion exchange membrane 150 coupled to the reference conduit distal end 142. The ion exchange membrane 150 can be configured to obstruct the reference conduit second opening 116 such that microorganisms within the sample 102 do not enter the reference conduit cavity 112. However, the ion exchange membrane 150 can allow ions to traverse the ion exchange membrane 150 to maintain a charge balance.

In some embodiments, the ion exchange membrane 150 can be a perfluoro-sulfonated ionomer membrane. As a more specific example, the ion exchange membrane 150 can be a Nafion® membrane provided by E.I. du Pont de Nemours and Company. Also, for example, the ion exchange membrane 150 can be an Aciplex® membrane provided by Asahi Kasei Corporation or a Flemion® membrane provided by AGC Chemicals Americas, Inc.

In some embodiments, the ion exchange membrane 150 can have a thickness of about 25 µm to about 180 µm. More specifically, the ion exchange membrane 150 can have a thickness of about 25 µm to about 100 µm. The ion exchange membrane 150 can also have a thickness of about 100 µm to about 180 µm.

In other embodiments, the ion exchange membrane 150 can have a thickness of about 180 µm to about 200 µm. For example, the ion exchange membrane 150 can have a thickness of about 183 µm.

The reference conduit cavity 112 can be at least partially filled with a reference buffer solution 152. The reference buffer solution 152 can be an aqueous redox buffer solution.

In one embodiment, the reference buffer solution 152 can comprise deionized water, potassium hexacyanoferrate, dihydrogen phosphate, disodium hydrogen phosphate, or a combination thereof. For example, the reference buffer solution 152 can comprise about 95% to 99% (v/v %) of deionized water, about 0.1% to 0.9% (w/v %) of potassium hexacyanoferrate(III), about 0.1% to 0.9% (w/v %) of potassium hexacyanoferrate(II), less than about 0.5% (w/v %) of potassium dihydrogen phosphate, and less than about 0.5% (w/v %) of disodium hydrogen phosphate. As a more specific example, the reference buffer solution can be a 220 mV/pH 7 redox buffer solution (Product Code 51350060) provided by Mettler-Toledo AG.

In other embodiments, the reference buffer solution 152 can be an aqueous redox buffer solution comprising 3M KCl. As a more specific example, the reference buffer solution can be 3M KCl redox buffer solution (Material No. 63056165) provided by Mettler-Toledo AG.

In one embodiment, the reference conduit cavity 112 can be filled with about 100 µL of reference buffer solution 152. In another embodiment, the reference conduit cavity 112 can be filled with about 500 µL of reference buffer solution 152. In other embodiments, the reference conduit cavity 112 can be filled with between about 100 µL to about 500 µL of reference buffer solution 152. In further embodiments, the reference conduit cavity 112 can be filled with between about 500 µL to about 1 mL of reference buffer solution 152. The amount of reference buffer solution 152 can depend on the volume of the reference conduit cavity 112, the size of the reference conduit 110, the size of the sample container 104, or a combination thereof.

The reference sensor component 108 can also comprise a reference electrode 120 extending into the reference conduit cavity 112 filled with the reference buffer solution 152. The reference electrode 120 can extend partially into the reference conduit cavity 112 filled with the reference buffer solution 152.

As a more specific example, the reference electrode 120 can comprise a reference electrode tip 144. The reference electrode tip 144 can be positioned proximal to the ion exchange membrane 150 when the reference electrode 120 is partially extended into the reference conduit cavity 112 filled with the reference buffer solution 152. More specifically, a volume of reference buffer solution 152 can separate the reference electrode tip 144 from the ion exchange membrane 150. The position of the reference electrode 120 within the reference conduit cavity 112 will be discussed in more detail in the following sections.

The reference electrode 120 can be made in part of one or more metals. In one embodiment, the reference electrode 120 can be made in part of platinum (Pt), stainless steel, or a combination thereof. In other embodiments, the reference electrode 120 can be made in part of another type of conductive metal. For example, the reference electrode 120 can be a metallic pin, wire, or rod inserted into the reference buffer solution 152 such that a segment of the reference electrode 120 (e.g., the reference electrode tip 144 and the segment of the reference electrode 120 in proximity to the reference electrode tip 144) is immersed in the reference buffer solution 152.

The sample 102 can be in fluid contact with the ion exchange membrane 150 such that the ion exchange membrane 150 acts as an interface of a salt bridge. Ions can diffuse from one side of the ion exchange membrane 150 to the other to maintain a charge balance.

The sensor apparatus 103 can also comprise an active sensor component 122 comprising an active electrode housing 124 extending into the sample chamber 106 configured to receive the sample 102. The active sensor component 122 can also comprise an active electrode 126 at least partially housed or surrounded by the active electrode housing 124.

The active electrode housing 124 can be made of an inert or non-conductive material. The active electrode housing 124 can comprise, a polymeric material such as polyvinyl chloride (PVC), poly(methyl methacrylate) (PMMA), polydimethylsiloxane (PDMS), a ceramic, silicon dioxide ($SiO_2$) or types of glass, or a combination thereof.

The active electrode 126 can comprise a sample contact surface 128. The active electrode 126 can be disposed at an active component distal end 130. The active electrode housing 124 can be configured to expose the sample contact surface 128 such that the sample contact surface 128 is in fluid communication with the sample 102.

In some embodiments, the active electrode 126 can be made in part of a metal oxide. For example, the active electrode 126 can be made in part of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

The active sensor component 122 can also comprise a conductive contact layer 132 coupled to the active electrode 126 and positioned proximal to the active electrode 126. The conductive contact layer 132 can also be housed within or encased by the active electrode housing 124.

The conductive contact layer 132 can be made in part of one or more metals. In some embodiments, the conductive contact layer 132 can be made in part of aluminum (Al), copper (Cu), platinum (Pt), or a combination thereof. The conductive contact layer 132 and the reference electrode 120 can be electrically coupled by conductive connections 134 or conductive traces to a voltmeter 136. The conductive connections 134 can be made in part of a conductive material. In one embodiment, the conductive connections 134 can be copper traces. For example, the conductive connections 134 can be electro-deposited copper, rolled annealed copper, high-ductility electro-deposited copper, or a combination thereof. In other embodiments, the conductive connections 134 can be made in part of silver or nickel.

In some embodiments, the voltmeter 136 can be a high-impedance voltmeter. The conductive connections 134 can electrically couple the active electrode 126 (via the conductive contact layer 132) and the reference electrode 120 to the voltmeter 136. The pH of the sample 102 can be measured based on a potential difference between the active electrode 126 and the reference electrode 120.

The sensor apparatus 103 can also comprise an aeration conduit 146. A segment of the aeration conduit 146 can extend into the sample chamber 106 such that a lumen or cavity within the aeration conduit 146 is in fluid communication with the sample chamber 106. The aeration conduit 146 can be configured to aerate the sample 102 received within the sample container 104. Aerating the sample 102 can enhance a growth rate of microorganisms within the sample 102 by increasing a supply of oxygen to such microorganisms. Moreover, aeration can also enable detachment of the microorganisms from the interior walls of the sample container 104 so as to inhibit biofilm formation.

Figure 1D:
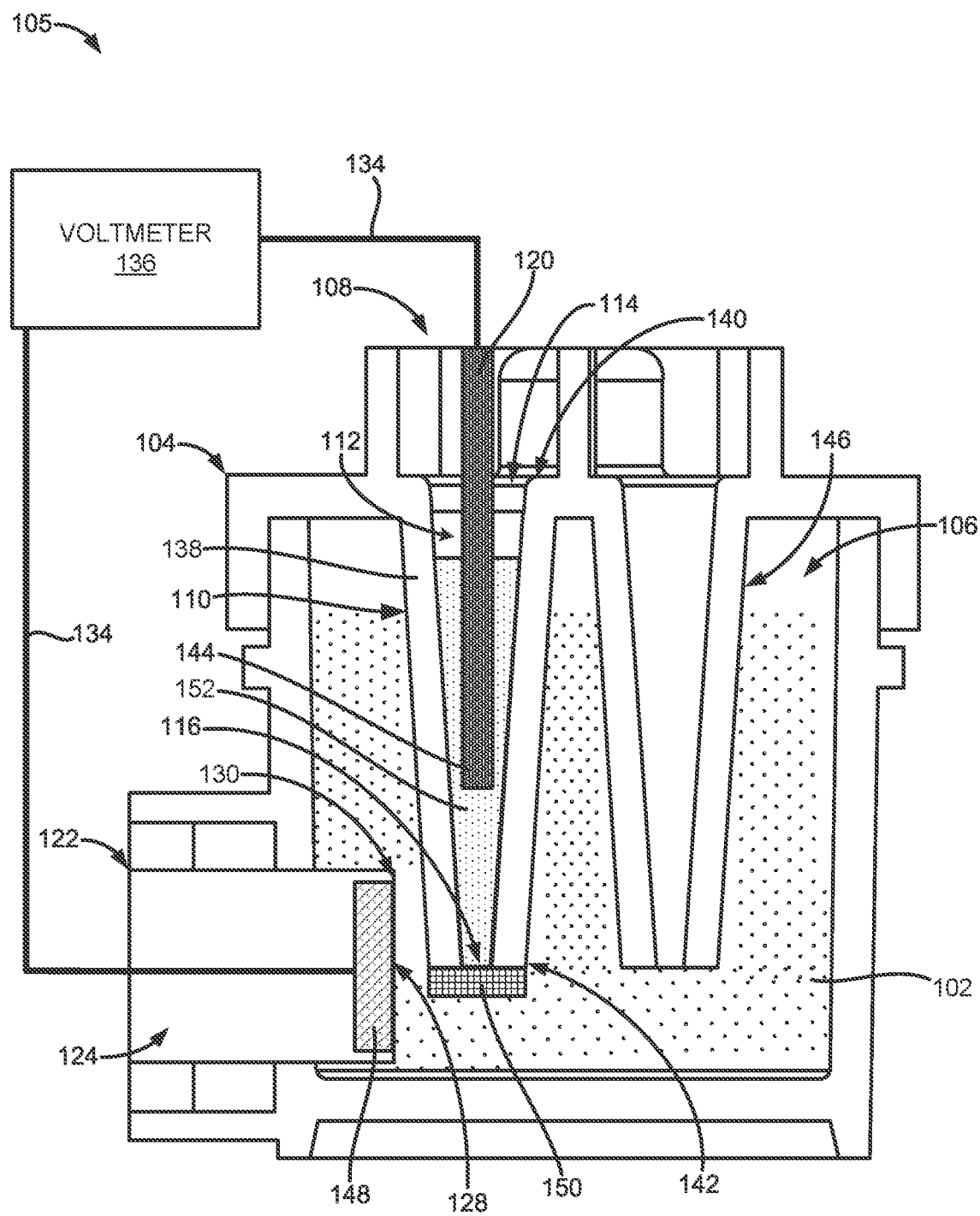
FIG. 1D illustrates another embodiment of a sensor apparatus for measuring an ORP of a sample.

FIG. 1D illustrates another embodiment of a sensor apparatus 105 for measuring the ORP of a sample 102. FIG. 1D illustrates a side cross-sectional view of the sensor apparatus 105.

The sensor apparatus 105 can comprise a sample container 104 having a sample chamber 106 configured to receive the sample 102. The sample 102 can be the same sample 102 discussed with respect to the sensor apparatus 100 (as shown in FIG. 1A), the sensor apparatus 101 (as shown in FIG. 1B), and the sensor apparatus 103 (as shown in FIG. 1C). The sample 102 can comprise a number of microorganisms or infectious agents. The apparatus, systems, and methods disclosed herein can be used to assay the sample 102 for microbial growth or lack thereof as part of a microbial quantification procedure or an antibiotic susceptibility testing (AST) procedure.

In some embodiments, an aqueous growth media can be added to the sample 102 prior to being introduced into the sample container 104. In other embodiments, the aqueous growth media can be added to the sample 102 once the sample 102 has been injected, delivered, or otherwise introduced into the sample container 104.

In one embodiment, the aqueous growth media can be a glucose supplemented Mueller Hinton broth (MHG). In other embodiments, the aqueous growth media can be a solution containing bacto-tryptone, tryptic soy digest, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose or other carbohydrates, or a combination thereof.

The sensor apparatus 105 can comprise a sample container 104 having a sample chamber 106 configured to receive the sample 102. The sample 102 can be the same sample 102 discussed with respect to the sensor apparatus 100 (as shown in FIG. 1A) and the sensor apparatus 101 (as shown in FIG. 1B). The sample 102 can comprise a number of microorganisms or infectious agents. The apparatus, systems, and methods disclosed herein can be used to assay the sample 102 for microbial growth or lack thereof as part of a microbial quantification procedure or an antibiotic susceptibility testing (AST) procedure.

The sample container 104 can be made in part of an inert or non-conductive material. In some embodiments, the sample container 104 can comprise or be made in part of a polymeric material, a ceramic material or glass, or a combination thereof. As a more specific example, the sample container 104 can comprise or be made in part of polyvinyl chloride (PVC), poly(methyl methacrylate) (PMMA), polydimethylsiloxane (PDMS), or a combination thereof.

The sensor apparatus 105 can also comprise a reference sensor component 108 and an active sensor component 122. The reference sensor component 108 can further comprise a reference conduit 110 comprising a reference conduit proximal end 140 defining a reference conduit first opening 114, a reference conduit distal end 142 defining a reference conduit second opening 116, and a reference conduit cavity 112 in between the reference conduit proximal end 140 and the reference conduit distal end 142.

The reference conduit 110 can comprise conduit walls 138 and the conduit walls 138 can taper from a reference conduit proximal end 140 to a reference conduit distal end 142. In one embodiment, the reference conduit 110 can be substantially shaped as a conic or frustoconic having a reference conduit cavity 112 also substantially shaped as a conic or frustoconic. In other embodiments, the reference conduit 110 can be substantially shaped as an elongate pyramid having a polygonal-shaped base. For example, the reference conduit 110 can be substantially shaped as an elongate triangular pyramid, square pyramid, or a pentagonal pyramid. In additional embodiments, the reference conduit 110 can be substantially shaped as a cylinder having a substantially cylindrical-shaped reference conduit cavity 112. In these embodiments, the reference conduit 110 can also have a tapered reference conduit distal end 142.

The reference conduit 110 can extend into the sample chamber 106 such that at least a portion of the reference conduit 110 is immersed in the sample 102 when the sample chamber 106 is filled with the sample 102. For example, the reference conduit distal end 142 can be immersed in the sample 102 within the sample chamber 106.

The reference sensor component 108 can comprise an ion exchange membrane 150 coupled to the reference conduit distal end 142. The ion exchange membrane 150 can be configured to obstruct the reference conduit second opening 116 such that microorganisms within the sample 102 do not enter the reference conduit cavity 112. However, the ion exchange membrane 150 can allow ions to traverse the ion exchange membrane 150 to maintain a charge balance.

In some embodiments, the ion exchange membrane 150 can be a perfluoro-sulfonated ionomer membrane. As a more specific example, the ion exchange membrane 150 can be a Nafion® membrane provided by E.I. du Pont de Nemours and Company. Also, for example, the ion exchange membrane 150 can be an Aciplex® membrane provided by Asahi Kasei Corporation or a Flemion® membrane provided by AGC Chemicals Americas, Inc.

In some embodiments, the ion exchange membrane 150 can have a thickness of about 25 μm to about 180 μm. More specifically, the ion exchange membrane 150 can have a thickness of about 25 μm to about 100 μm. The ion exchange membrane 150 can also have a thickness of about 100 μm to about 180 μm.

In other embodiments, the ion exchange membrane 150 can have a thickness of about 180 μm to about 200 μm. For example, the ion exchange membrane 150 can have a thickness of about 183 μm.

The reference conduit cavity 112 can be at least partially filled with a reference buffer solution 152. The reference buffer solution 152 can be an aqueous redox buffer solution.

In one embodiment, the reference buffer solution 152 can comprise deionized water, potassium hexacyanoferrate, dihydrogen phosphate, disodium hydrogen phosphate, or a combination thereof. For example, the reference buffer solution 152 can comprise about 95% to 99% (v/v %) of deionized water, about 0.1% to 0.9% (w/v %) of potassium hexacyanoferrate(III), about 0.1% to 0.9% (w/v %) of potassium hexacyanoferrate(II), less than about 0.5% (w/v %) of potassium dihydrogen phosphate, and less than about 0.5% (w/v %) of disodium hydrogen phosphate. As a more specific example, the reference buffer solution can be a 220 mV/pH 7 redox buffer solution (Product Code 51350060) provided by Mettler-Toledo AG.

In other embodiments, the reference buffer solution 152 can be an aqueous redox buffer solution comprising 3M KCl. As a more specific example, the reference buffer solution can be 3M KCl redox buffer solution (Material No. 63056165) provided by Mettler-Toledo AG.

In one embodiment, the reference conduit cavity 112 can be filled with about 100 µL of reference buffer solution 152. In another embodiment, the reference conduit cavity 112 can be filled with about 500 µL of reference buffer solution 152. In other embodiments, the reference conduit cavity 112 can be filled with between about 100 µL to about 500 µL of reference buffer solution 152. In further embodiments, the reference conduit cavity 112 can be filled with between about 500 µL to about 1 mL of reference buffer solution 152. The amount of reference buffer solution 152 can depend on the volume of the reference conduit cavity 112, the size of the reference conduit 110, the size of the sample container 104, or a combination thereof.

The reference sensor component 108 can also comprise a reference electrode 120 extending into the reference conduit cavity 112 filled with the reference buffer solution 152. The reference electrode 120 can extend partially into the reference conduit cavity 112 filled with the reference buffer solution 152.

As a more specific example, the reference electrode 120 can comprise a reference electrode tip 144. The reference electrode tip 144 can be positioned proximal to the ion exchange membrane 150 when the reference electrode 120 is partially extended into the reference conduit cavity 112 filled with the reference buffer solution 152. More specifically, a volume of reference buffer solution 152 can separate the reference electrode tip 144 from the ion exchange membrane 150. The position of the reference electrode 120 within the reference conduit cavity 112 will be discussed in more detail in the following sections.

The reference electrode 120 can be made in part of one or more metals. In one embodiment, the reference electrode 120 can be made in part of platinum (Pt), stainless steel, or a combination thereof. In other embodiments, the reference electrode 120 can be made in part of another type of conductive metal. For example, the reference electrode 120 can be a metallic pin, wire, or rod inserted into the reference buffer solution 152 such that a segment of the reference electrode 120 (e.g., the reference electrode tip 144 and the segment of the reference electrode 120 in proximity to the reference electrode tip 144) is immersed in the reference buffer solution 152.

The sample 102 can be in fluid contact with the ion exchange membrane 150 such that the ion exchange membrane 150 acts as an interface of a salt bridge. Ions can diffuse from one side of the ion exchange membrane 150 to the other to maintain a charge balance.

The sensor apparatus 105 can also comprise an active sensor component 122 comprising an active electrode housing 124 extending into the sample chamber 106 configured to receive the sample 102. The active sensor component 122 can also comprise an active electrode 148 at least partially housed or surrounded by the active electrode housing 124.

The active electrode housing 124 can be made of an inert or non-conductive material. The active electrode housing 124 can comprise, a polymeric material such as polyvinyl chloride (PVC), poly(methyl methacrylate) (PMMA), polydimethylsiloxane (PDMS), a ceramic, silicon dioxide ($SiO_2$) or types of glass, or a combination thereof.

The active electrode 148 can comprise a sample contact surface 128. The active electrode 148 can be disposed at an active component distal end 130. The active electrode housing 124 can be configured to expose the sample contact surface 128 such that the sample contact surface 128 is in fluid communication with the sample 102.

In some embodiments, the active electrode 148 can be made in part of one or more metals, one or more metal oxides, or a combination thereof. For example, the active electrode 148 can be made in part of platinum (Pt), gold (Au), a redox sensitive metal oxide, or a combination thereof. In some embodiments, the redox sensitive metal oxide can comprise silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

The active electrode 148 and the reference electrode 120 can be electrically coupled by conductive connections 134 or conductive traces to a voltmeter 136. The conductive connections 134 can be made in part of a conductive material. In one embodiment, the conductive connections 134 can be copper traces. For example, the conductive connections 134 can be electro-deposited copper, rolled annealed copper, high-ductility electro-deposited copper, or a combination thereof. In other embodiments, the conductive connections 134 can be made in part of silver or nickel.

In some embodiments, the voltmeter 136 can be a high-impedance voltmeter. The ORP of the sample 102 can be measured based on a potential difference between the active electrode 148 and the reference electrode 120.

The sensor apparatus 105 can also comprise an aeration conduit 146. A segment of the aeration conduit 146 can extend into the sample chamber 106 such that a lumen or cavity within the aeration conduit 146 is in fluid communication with the sample chamber 106. The aeration conduit 146 can be configured to aerate the sample 102 received within the sample container 104. Aerating the sample 102 can enhance a growth rate of microorganisms within the sample 102 by increasing a supply of oxygen to such microorganisms. Moreover, aeration can also enable detachment of the microorganisms from the interior walls of the sample container 104 so as to inhibit biofilm formation.

Figure 2:
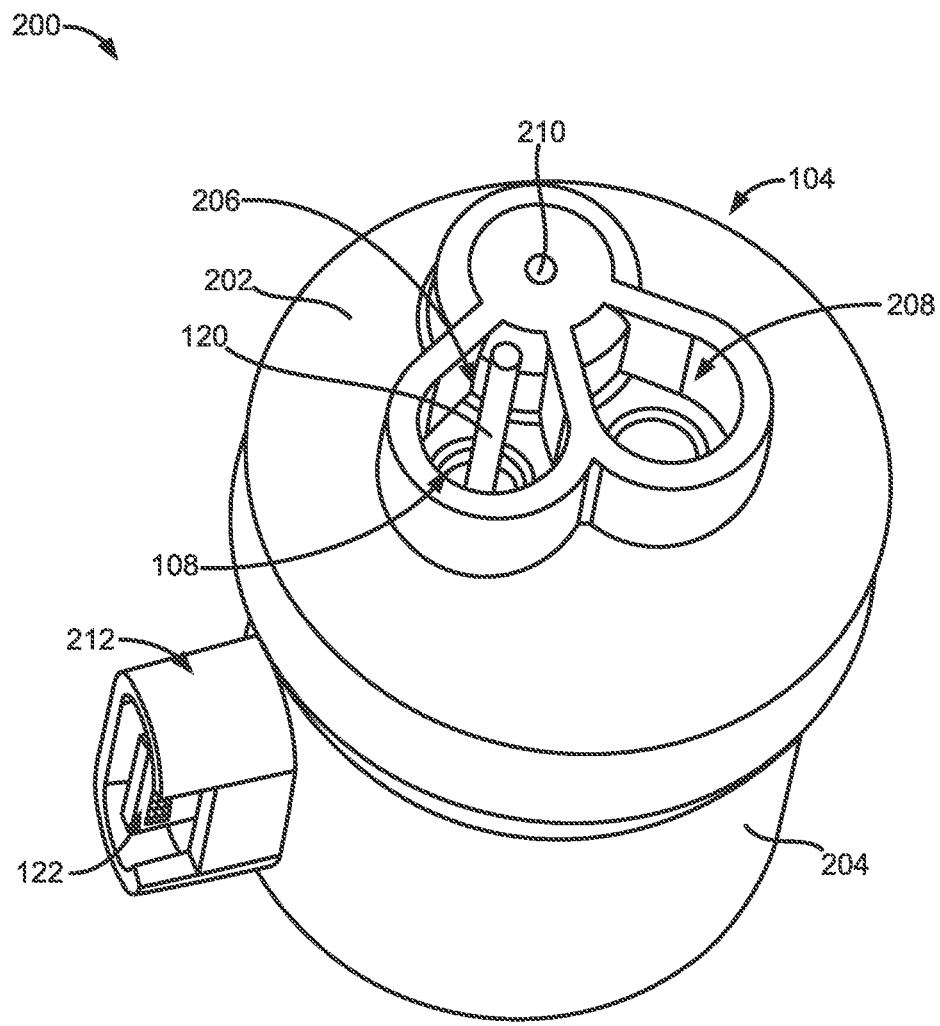
FIG. 2 illustrates a top perspective view of an embodiment of a sensor apparatus.

FIG. 2 illustrates a top perspective view of an embodiment of a sensor apparatus 200. The sensor apparatus 200 can be or refer to any of the previously described sensors including the sensor apparatus 100 of FIG. 1A, the sensor apparatus 101 of FIG. 1B, the sensor apparatus 103 of FIG. 1C, and the sensor apparatus 105 of FIG. 1D.

As shown in FIG. 2, the sample container 104 can comprise a container cap 202 coupled to a container body 204. In one embodiment, the container body 204 can be a substantially cylindrical-shaped container or vessel. In other embodiments, the container body 204 can be a substantially cuboidal-, pyramidal-, or conical-shaped container or vessel. The container cap 202 can have a shape configured to couple or attach to the container body 204.

In one embodiment, the container cap 202 can be coupled to the sample container 104 via a screw-on threaded connection. In other embodiments, the container cap 202 can be coupled to the sample container 104 via clasps, latches, an interference fit, or a combination thereof. The container cap 202 can be uncoupled or detached from the container body 204 to allow a user (e.g., a clinician or lab technician) to dispense the sample 102 into the sample chamber 106 of the sample container 104.

In one embodiment, the container cap 202 can have a reference port 206 defined along a surface of the container cap 202. The reference port 206 can be an opening or channel defined on the surface of the container cap 202.

In some embodiments, the reference conduit 110 can be integrated with the container cap 202 such that separating the container cap 202 from the container body 204 also removes the reference conduit 110 from the sample chamber 106. In these and other embodiments, the reference port 206 can be an opening or channel that provides access to the reference conduit cavity 112. For example, the reference electrode 120 can be inserted or otherwise extended into the reference conduit cavity 112 through the reference port 206 and the reference conduit first opening 114.

In other embodiments, the entire reference sensor component 108, including the reference conduit 110, can be removably coupled to the sample container 104 such that the entire reference sensor component 108 is detachable from the sample container 104. For example, the reference conduit 110 can be removably coupled to the container cap 202. In these and other embodiments, the reference port 206 can provide access to the sample chamber 106. The reference conduit 110 (comprising either the reference buffer gel 118 or the reference buffer solution 152) can be inserted or otherwise extended through the reference port 206. The reference conduit 110 can then be coupled to the sample container 104 (e.g., the container cap 202) via an interference fit, a threaded connection, clasps, or a combination thereof. The reference electrode 120 can then be inserted or otherwise extended into the reference conduit cavity 112 through the reference port 206 and the reference conduit first opening 114.

FIG. 2 illustrates that the container cap 202 can also have an aeration port 208 defined along a surface of the container cap 202. The aeration port 208 can provide access to the aeration conduit 146 (see any of FIG. 1A, FIG. 1B, FIG. 1C, or FIG. 1D). For example, an aeration tube or hose can be inserted into the aeration conduit 146 through the aeration port 208 to aerate the sample 102 within the sample container 104.

The container cap 202 can also have a vent port 210 defined along a surface of the container cap 202. The vent port 210 can allow excess air or gaseous byproducts produced by the microorganisms within the sample container 104 to evacuate from the sample chamber 106.

The sample container 104 can also comprise a lateral port 212 defined along a lateral surface of the container body 204. The lateral port 212 can be an opening or channel providing access to the sample chamber 106. At least part of the active sensor component 122 can extend through the lateral port 212 when coupled to the sample container 104. In some embodiments, the active sensor component 122 can also be detachably coupled to the sample container 104 such that new instances of the active sensor component 122 can replace old or used instances of the active sensor component 122.

Figures 3A, 3B:
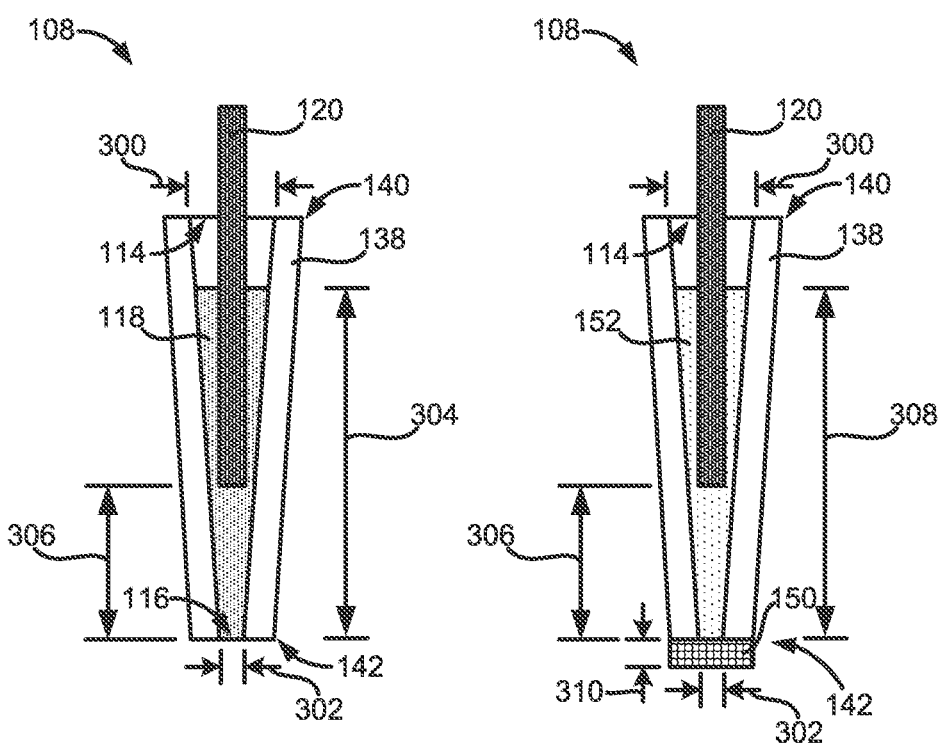
FIG. 3A illustrates a side cross-sectional view of an embodiment of a reference sensor component.
FIG. 3B illustrates a side cross-sectional view of another embodiment of a reference sensor component.

FIG. 3A illustrates a side cross-sectional view of an embodiment of a reference sensor component 108. The reference sensor component 108 shown in FIG. 3A can be used as part of the sensor apparatus 100 of FIG. 1A or the sensor apparatus 101 of FIG. 1B.

The reference conduit 110 can comprise conduit walls 138 that taper from a reference conduit proximal end 140 to a reference conduit distal end 142. Moreover, the reference conduit proximal end 140 can define a first opening area that is larger than a second opening area defined by the reference conduit distal end 142. For example, the first opening area can be about 19 mm$^2$ to about 80 mm$^2$ and the second opening area can be about 0.79 mm$^2$ to about 3.14 mm$^2$.

In the example embodiment shown in FIG. 3A, the reference conduit 110 can be substantially shaped as an elongate upside-down frustoconic. In this embodiment, both the reference conduit first opening 114 and the reference conduit second opening 116 can be substantially circular-shaped and defined by a first opening diameter 300 and a second opening diameter 302, respectively. In some instances, the first opening diameter 300 can be about 5.00 mm to about 10.0 mm. The second opening diameter 302 can be about 1.00 mm to about 5.00 mm.

FIG. 3A also illustrates that the reference buffer gel 118 can be filled up to a gel height 304 of about 5.00 mm to about 20.0 mm. The gel height 304 can vary depending on the volume of the reference conduit cavity 112. As previously discussed, the reference conduit cavity 112 can be filled with about 100 μL of reference buffer gel 118. In another embodiment, the reference conduit cavity 112 can be filled with about 500 μL of reference buffer gel 118. In other embodiments, the reference conduit cavity 112 can be filled with between about 100 μL to about 500 μL of reference buffer gel 118. In further embodiments, the reference conduit cavity 112 can be filled with between about 500 μL to about 1 mL of reference buffer gel 118. The amount of reference buffer gel 118 can be optimized to achieve a predetermined reference time. For example, in some instances, the amount of reference buffer gel 118 can be optimized to achieve a reference time between 3.0 hours to 6.0 hours.

The reference electrode 120 can also be separated from the reference conduit second opening 116 by a separation distance 306. In one embodiment, the separation distance can be about 1.0 mm. In another embodiment, the separation distance 306 can be about 5.0 mm. In other embodiments, the separation distance 306 can be between about 1.0 mm and 5.0 mm.

FIG. 3B illustrates a side cross-sectional view of another embodiment of a reference sensor component 108. The reference sensor component 108 shown in FIG. 3B can be used as part of the sensor apparatus 103 of FIG. 1C or the sensor apparatus 105 of FIG. 1D.

The reference conduit 110 can comprise conduit walls 138 that taper from a reference conduit proximal end 140 to a reference conduit distal end 142. Moreover, the reference conduit proximal end 140 can define a first opening area that is larger than a second opening area defined by the reference conduit distal end 142. For example, the first opening area can be about 19 mm$^2$ to about 80 mm$^2$ and the second opening area can be about 0.79 mm$^2$ to about 3.14 mm$^2$.

In the example embodiment shown in FIG. 3B, the reference conduit 110 can be substantially shaped as an elongate upside-down frustoconic. In this embodiment, both the reference conduit first opening 114 and the reference conduit second opening 116 can be substantially circular-shaped and defined by a first opening diameter 300 and a second opening diameter 302, respectively. In some instances, the first opening diameter 300 can be about 5.00 mm to about 10.0 mm. The second opening diameter 302 can be about 1.00 mm to about 5.00 mm.

FIG. 3B also illustrates that the reference buffer solution 152 can be filled up to a solution height 308 of about 5.00 mm to about 20.0 mm. The solution height 308 can vary depending on the volume of the reference conduit cavity 112. As previously discussed, the reference conduit cavity 112 can be filled with about 100 μL of reference buffer solution 152. In another embodiment, the reference conduit cavity 112 can be filled with about 500 μL of reference buffer solution 152. In other embodiments, the reference conduit cavity 112 can be filled with between about 100 μL to about 500 μL of reference buffer solution 152. In further embodiments, the reference conduit cavity 112 can be filled with between about 500 μL to about 1 mL of reference buffer solution 152. The amount of reference buffer solution 152 can be optimized to achieve a predetermined reference time. For example, in some instances, the amount of reference buffer solution 152 can be optimized to achieve a reference time between 3.0 hours to 6.0 hours.

The reference electrode 120 can also be separated from the ion exchange membrane 150 by a separation distance 306. In one embodiment, the separation distance can be about 1.0 mm. In another embodiment, the separation distance 306 can be about 5.0 mm. In other embodiments, the separation distance 306 can be between about 1.0 mm and 5.0 mm.

The ion exchange membrane 150 can have a membrane thickness 310 of about 25 μm to about 180 μm. More specifically, the ion exchange membrane 150 can have a membrane thickness 310 of about 25 μm to about 100 μm. The ion exchange membrane 150 can also have a membrane thickness 310 of about 100 μm to about 180 μm.

Figure 4:
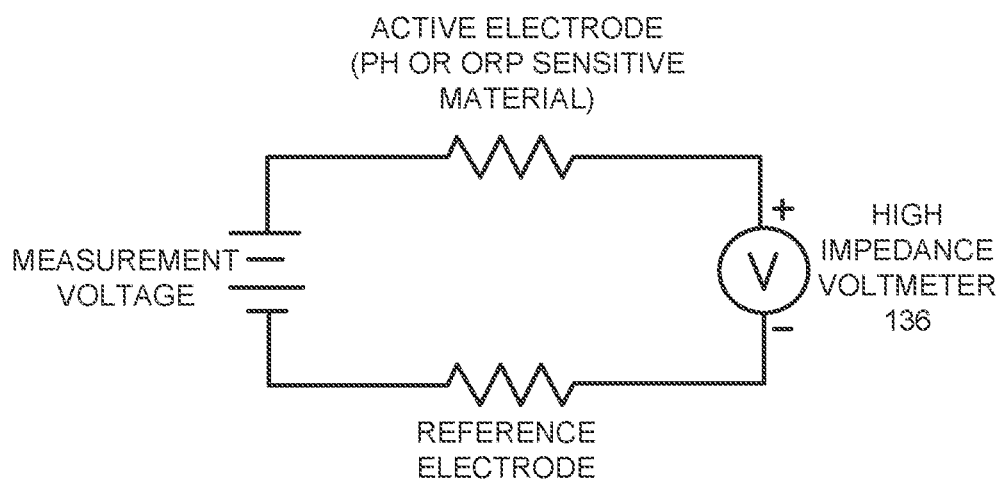
FIG. 4 illustrates a schematic of an active electrode and a reference electrode of the sensor apparatus connected to a high impedance voltmeter.

FIG. 4 illustrates a schematic of an active electrode (e.g., the active electrode 126 or the active electrode 148) and a reference electrode (e.g., the reference electrode 120) electrically coupled to a high impedance voltmeter (e.g., voltmeter 136). As previously discussed, the reference sensor component 108 can be configured such that either the reference buffer gel 118 or the ion exchange membrane 150 is in fluid contact (or solid-to-liquid contact) with the sample 102 within the sample container 104. In addition, the active electrode (e.g., the active electrode 126 or the active electrode 148) can also be in fluid contact with the sample 102 within the sample container 104.

The reference electrode can be immersed or inserted into either the reference buffer gel 118 or the reference buffer solution 152 and electrically coupled to a high impedance voltmeter (e.g., voltmeter 136). The active electrode can also be electrically coupled to the same high impedance voltmeter via conductive connections 134. The reference electrode can serve as a stable half-cell potential compared to the active electrode and a potential difference between the active electrode and the reference electrode can be used to determine the pH or ORP of the sample 102.

Figure 5A:
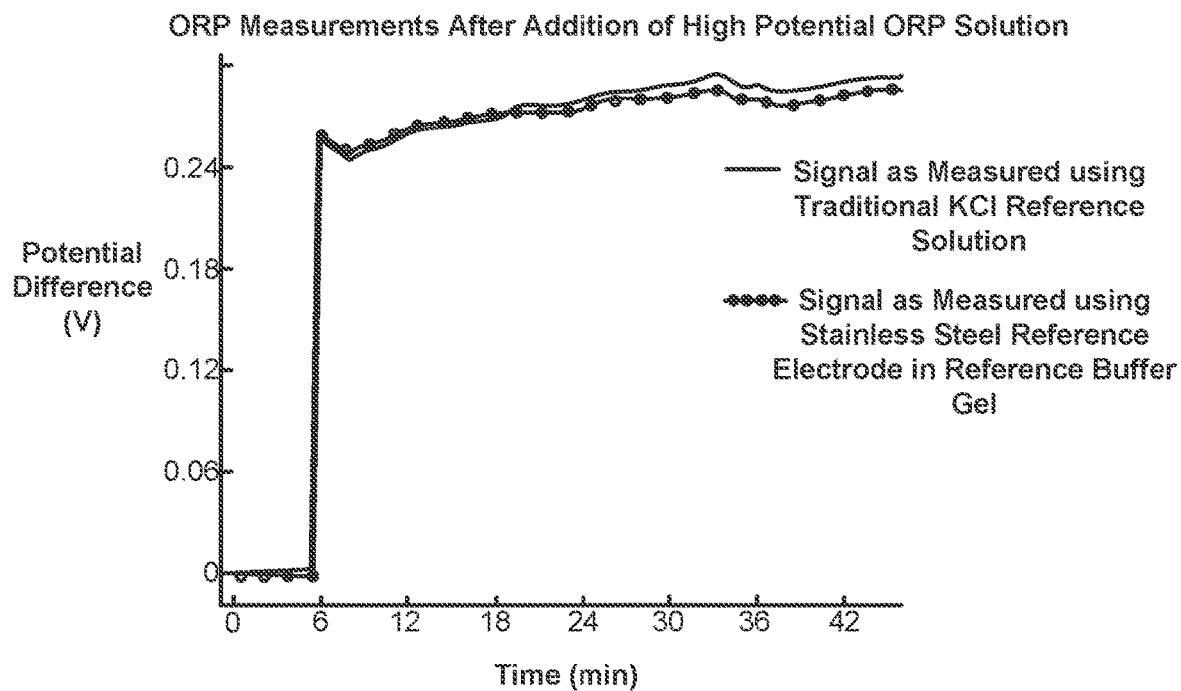
FIG. 5A illustrates ORP measurements made using a traditional KCl reference solution and a stainless steel reference electrode in a reference buffer gel after addition of a high potential ORP solution.

FIG. 5A is a graph illustrating ORP measurements made using a traditional KCl reference solution and a stainless steel reference electrode in a reference buffer gel after addition of a high potential ORP solution. To test the efficacy of the sensor apparatus 101 (see FIG. 1B), a known high potential ORP solution (e.g., an aqueous mixture comprising Virkon™ powder) was added to an ORP buffer solution (e.g., a 220 mV/pH 7 ORP buffer solution). The resulting change in the potential difference was measured with both a traditional ORP probe (e.g., a Mettler Toledo™ ORP probe provided by Mettler-Toledo AG) using a traditional KCl reference solution and the sensor apparatus 101 comprising a stainless steel reference electrode 120 immersed in the reference buffer gel 118. Both the traditional ORP probe and the sensor apparatus 101 used the same platinum (Pt) active electrode. As shown in FIG. 5A, both sensor setups behaved similarly in response to the addition of the known high potential ORP solution. The reference sensor component 108 comprising the reference buffer gel 118 maintained a stable reference potential similar to the traditional KCl reference in the traditional ORP probe.

Figure 5B:
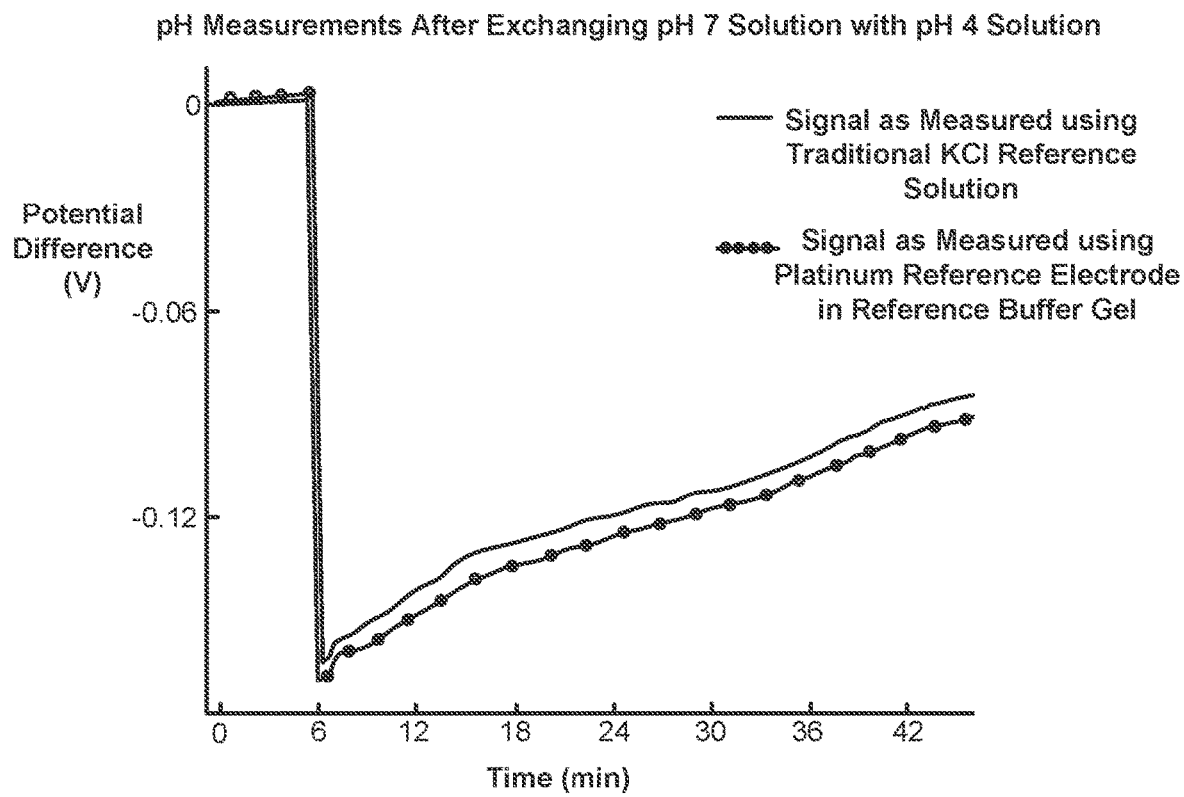
FIG. 5B illustrates pH measurements made using a traditional KCl reference solution and a platinum reference electrode in a reference buffer gel after exchanging a pH 7 solution with a pH 4 solution.

FIG. 5B is a graph illustrating pH measurements made using a traditional KCl reference solution and a platinum reference electrode in a reference buffer gel after exchanging a pH 7 solution with a pH 4 solution. To test the efficacy of the sensor apparatus 100 (see FIG. 1A), a pH change was induced by replacing a pH 7 solution with a pH 4 solution. The resulting change in the potential difference was measured with both a traditional pH probe (e.g., a Mettler Toledo™ pH probe provided by Mettler-Toledo AG) using a traditional KCl reference solution and the sensor apparatus 100 comprising a platinum reference electrode 120 immersed in the reference buffer gel 118. Both the traditional pH probe and the sensor apparatus 100 used the same iridium dioxide ($IrO_2$) active electrode. As shown in FIG. 5B, both sensor setups behaved similarly in response to the pH step change. The reference sensor component 108 comprising the reference buffer gel 118 showed a similar sensitivity and step height as the traditional pH probe with the KCl reference solution.

Figure 6:
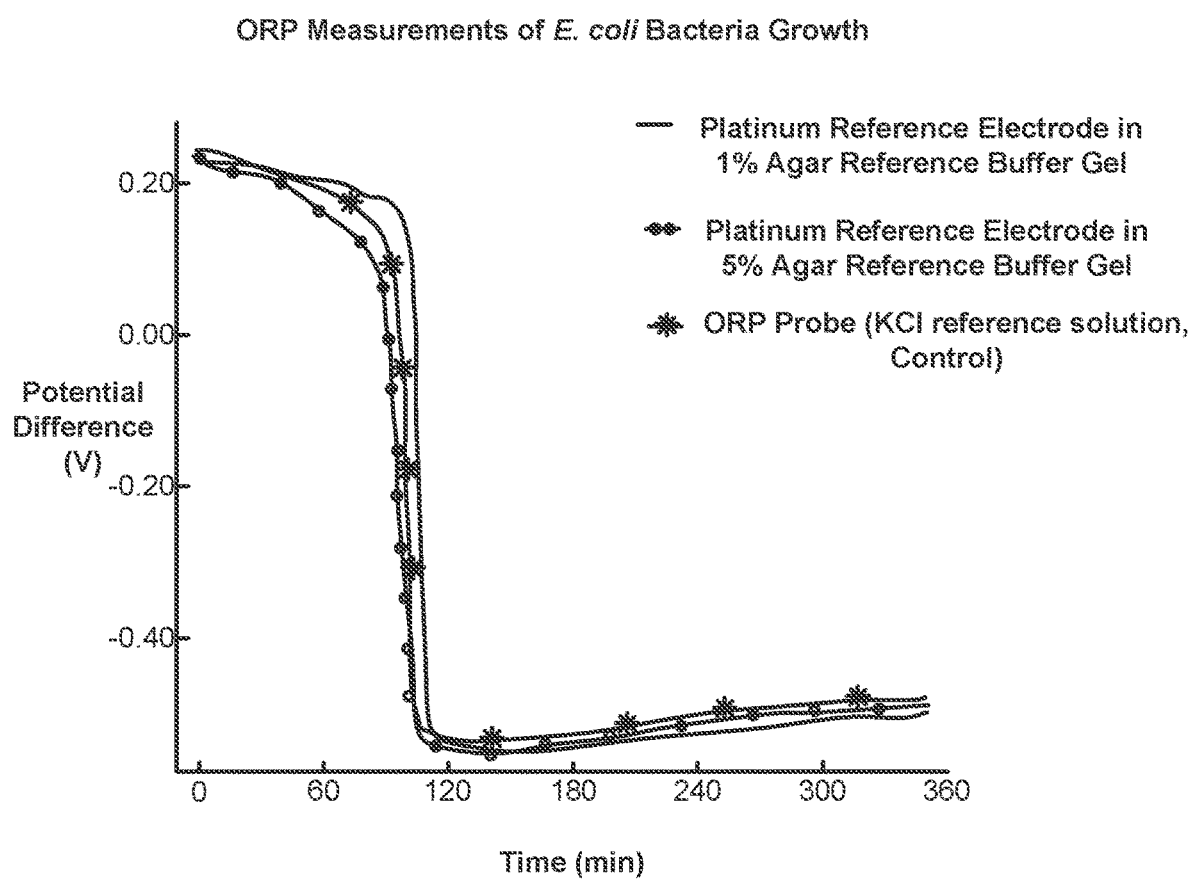
FIG. 6 illustrates ORP measurements of E. coli bacterial growth using a reference electrode in 1% agar gel buffer, 5% agar gel buffer, and a traditional KCl reference solution.

FIG. 6 is a graph illustrating ORP measurements of *E. coli* bacterial growth using a reference electrode in 1% agar gel buffer, 5% agar gel buffer, and a traditional KCl reference solution. As indicated in FIG. 6, the ORP of a solution comprising *E. coli* was monitored using a traditional ORP probe with a traditional KCl reference solution and also with two instances of the sensor apparatus 101. In the first instance, the reference buffer gel 118 contained 1% (w/v %) of agar powder. In the second instance, the reference buffer gel 118 contained 5% (w/v %) of agar powder. All three sensor setups used the same platinum (Pt) active electrode. As shown in FIG. 6, all three sensor setups behaved similarly and produced similar growth curves. Any difference in signal timing was within the variability of the three platinum (Pt) active electrodes.

Figure 7A:
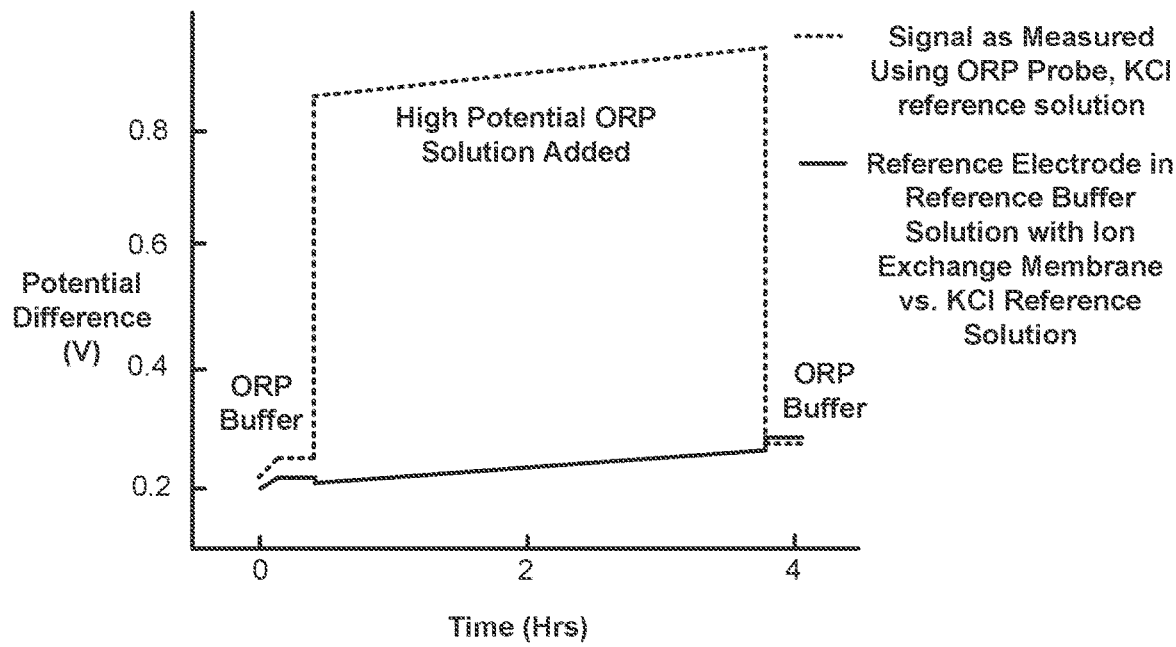
FIG. 7A illustrates certain ORP measurements made when a traditional ORP buffer solution is replaced with a high potential ORP solution and then switched back to the traditional ORP buffer solution.

FIG. 7A is a graph illustrating certain ORP measurements made when a traditional ORP buffer solution was replaced with a high potential ORP solution (e.g., a Virkon™ solution) and then switched back to the traditional ORP buffer solution. The dashed line indicates an ORP signal measured using a traditional ORP probe with a traditional KCl reference solution. As anticipated, the ORP signal measured by the ORP probe spikes when the traditional ORP buffer solution is replaced with the high potential ORP solution and drops down again when the high potential ORP solution is switched back to the traditional ORP buffer solution.

The solid line indicates a measurement of the potential difference between a traditional reference sensor component comprising a traditional KCl reference solution and a reference sensor component comprising an ion exchange membrane 150 (e.g., Nafion™ membrane). As shown in FIG. 7A, the potential difference between the traditional reference sensor component and the reference sensor component comprising the ion exchange membrane 150 remain unchanged even when the ORP buffer solution was replaced with the high potential ORP solution.

Figure 7B:
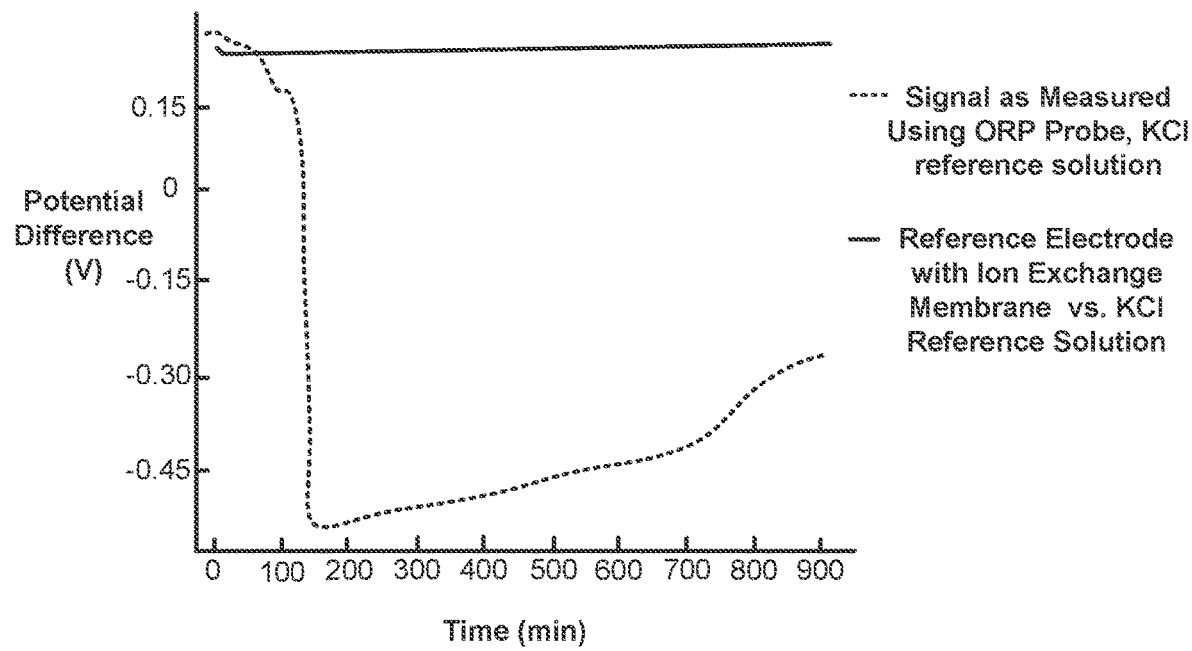
FIG. 7B illustrates ORP measurements of E. coli bacterial growth using a traditional ORP probe and a potential difference between a reference sensor component with an ion exchange membrane and a KCl reference solution during the measurement period.

FIG. 7B is a graph illustrating ORP measurements of *E. coli* bacterial growth using a traditional ORP probe and a potential difference between a reference sensor component with an ion exchange membrane and a traditional reference sensor component with a KCl reference solution. As indicated in FIG. 7B, the ORP of a solution comprising *E. coli* was monitored using a traditional ORP probe with a traditional KCl reference solution. The dashed line in FIG. 7B indicates the results of such a measurement. The solid line in FIG. 7B indicates a potential difference between the traditional KCl reference solution and a reference sensor component comprising the ion exchange membrane 150. As shown in FIG. 7B, the potential difference remained unchanged during the *E. coli* growth period. (even up to 15 hours).

Figure 8:
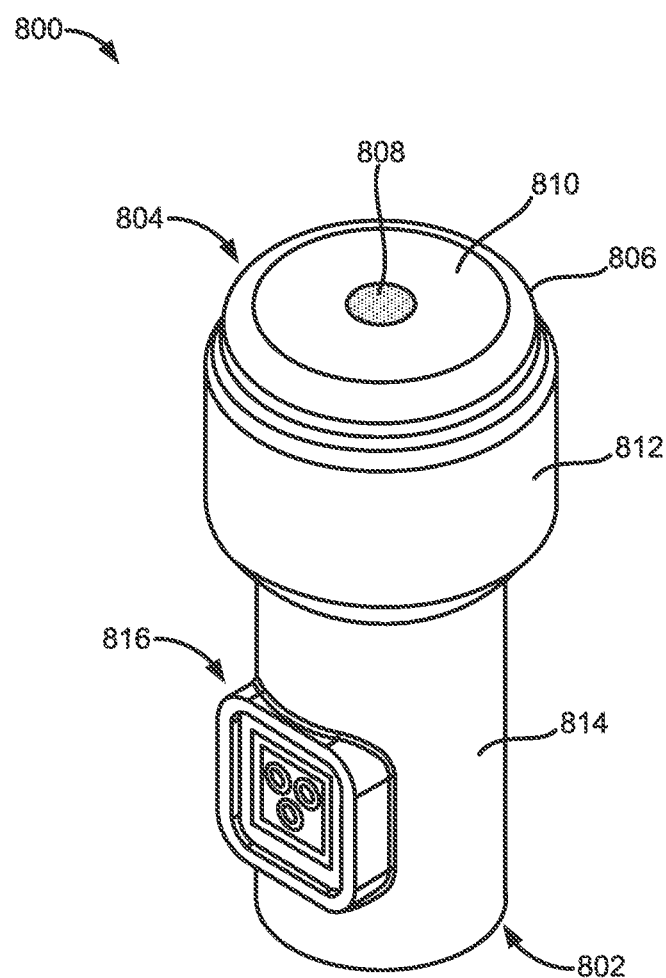
FIG. 8 illustrates another embodiment of a sensor apparatus for measuring a solution characteristic of a sample.

FIG. 8 illustrates another embodiment of a sensor apparatus 800 for measuring a solution characteristic (e.g., pH or ORP) of the sample 102. The sensor apparatus 800 can comprise a sample container 802 having a sample chamber 908 (see, for example, FIG. 9A) defined therein. The sample chamber 908 can be configured to receive the sample 102. The sensor apparatus 800 can also comprise a reference sensor component 804. In some embodiments, the reference sensor component 804 can be fabricated as part of a container cap 806 configured to cover an open end of the sample container 802.

In some embodiments, the sample container 802 can be a cuvette. In other embodiments, the sample container 802 can be a diagnostic tube, a part of a test tube, a glass container, or another type of laboratory container or vessel.

In certain embodiments contemplated by this disclosure, the sample container 802 can refer to a sample well of a well plate. The well plate can be a custom well plate having deeper wells than a conventional well plate or microtiter plate.

Figure 9A:
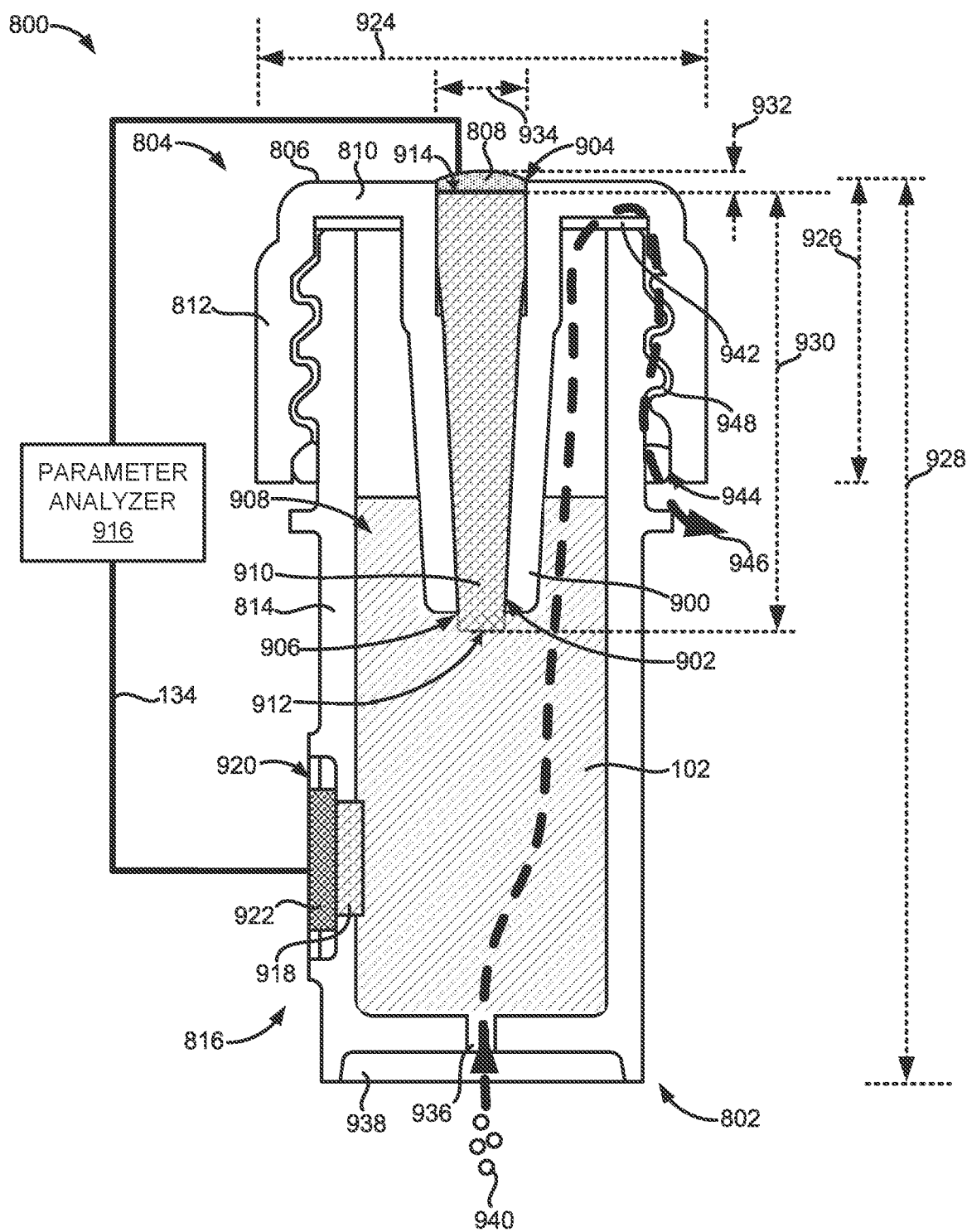
FIG. 9A illustrates a side cross-sectional view of another embodiment of a sensor apparatus.
Figure 9B:
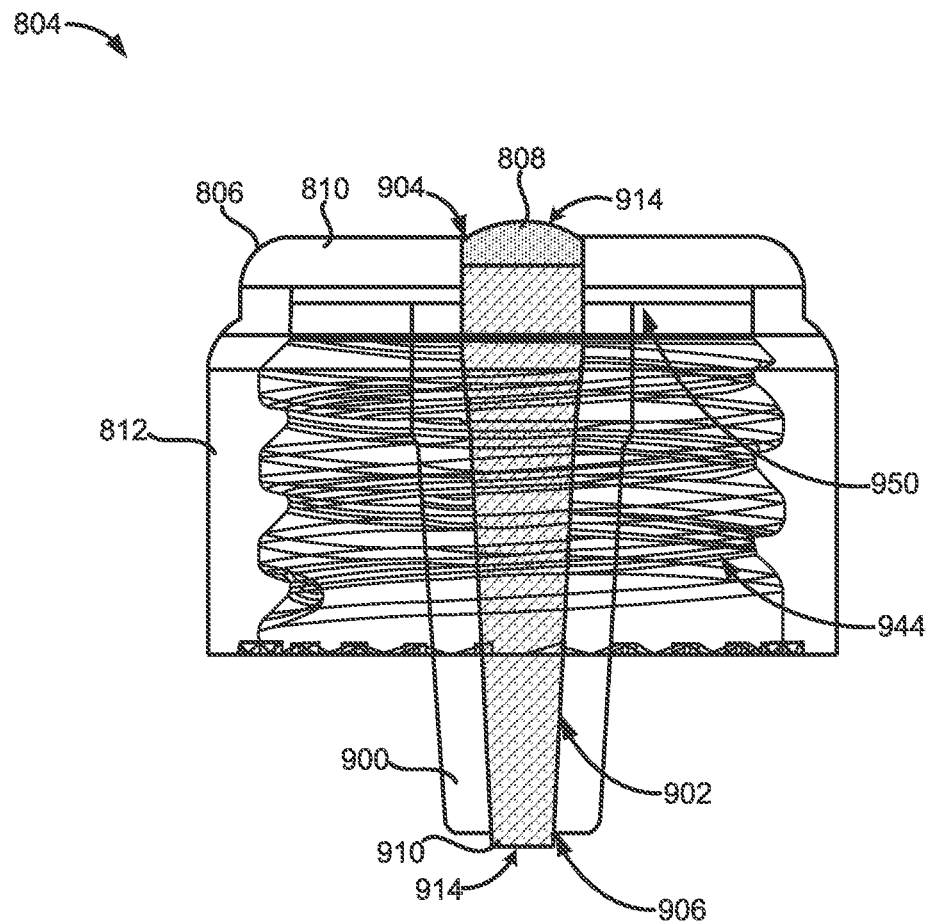
FIG. 9B illustrates an embodiment of a reference sensor component.

The reference sensor component 804 can comprise a reference conduit 900 comprising a reference conduit cavity 902, a reference conduit first opening 904, and a reference conduit second opening 906 (see, for example, FIGS. 9A and 9B). The reference conduit 900 can be an elongate channel or passageway configured to extend into the sample chamber 908 of the sample container 802.

The sensor apparatus 800 can also comprise a wicking component 910 (see, for example, FIGS. 9A and 9B) positioned within the reference conduit cavity 902 and extending through a length of the reference conduit cavity 902. The wicking component 910 and the reference conduit cavity 902 will be discussed in more detail in the following sections.

The sensor apparatus 800 can further comprise a reference electrode material 808 disposed at a proximal end of the wicking component 910. When the reference sensor component 804 is fabricated as a container cap 806, the reference electrode material 808 can protrude or extend through a cap top 810 of the container cap 806 such that the reference electrode material 808 is accessible and visible through the cap top 810 of the container cap 806. For example, an opening can be defined along the cap top 810 of the container cap 806 and the reference electrode material 808 can protrude or extend through the opening defined along the cap top 810 of the container cap 806. In other embodiments not shown in the figures but contemplated by this disclosure, the reference electrode material 808 can protrude through a lateral side 812 or corner of the container cap 806.

When the reference sensor component 804 is fabricated as a container cap 806, the container cap 806 can be removably attached or coupled to the sample container 802. For example, the container cap 806 can be removably attached or coupled to the sample container 802 via a threaded connection 944 (see FIGS. 9A and 9B). In other embodiments, the container cap 806 can be removably attached or coupled to the sample container 802 via an interference fit, a press fit (e.g., a tapered press fit, an expansion press fit, etc.), a snap fit, latches, or a combination thereof.

In these and other embodiments, the container cap 806 can fit over or cover a portion (e.g., a proximal portion) of the sample container 802. In these embodiments, the lateral sides 812 of the container cap 806 can extend radially beyond container walls 814 of the sample container 802. In instances where the sample container 802 is substantially cylindrical-shaped and the shape of the container cap 806 accommodates the shape of the sample container 802, an outer circumference (or circular footprint) of the container cap 806 can be greater than an outer circumference (or circular footprint) of the sample container 802.

The sensor apparatus 800 can also comprise an active sensor component 816. The active sensor component 816 can be positioned or otherwise disposed along a container wall 814 of the sample container 802. The active sensor component 816 will be discussed in more detail in the following sections. The reference sensor component 804 and the active sensor component 816 can be electrically coupled by conductive connections to a parameter analyzer 916 (see, for example, FIG. 9A). The solution characteristic of the sample 102 can be determined based on a potential difference measured between an active electrode material 918 (see, for example, FIG. 9A) of the active sensor component 816 and the reference electrode material 808.

In some embodiments, the solution characteristic measured or monitored using the sensor apparatus 800 can be a pH of the sample 102 and at least part of the active sensor component 816 can be made in part of a pH-sensitive material. The pH-sensitive material can comprise at least one of silicon dioxide, aluminum oxide, titanium dioxide, tantalum pentoxide, hafnium dioxide, iridium dioxide, ruthenium dioxide, and zirconium dioxide.

In these and other embodiments, the solution characteristic measured or monitored using the sensor apparatus 800 can be an oxidation reduction potential (ORP) of the sample 102 and at least part of the active sensor component 816 can be made in part of a redox-sensitive material. The redox-sensitive material can comprise at least one of platinum, gold, silicon dioxide, aluminum oxide, titanium dioxide, tantalum pentoxide, hafnium dioxide, iridium dioxide, ruthenium dioxide, and zirconium dioxide.

As previously discussed, the sample 102 can comprise an infectious agent or microorganism (e.g., bacteria, fungi, etc.). The sensor apparatus 800 can be used to assay the sample 102 for microbial or infectious agent growth or lack thereof as part of a microbial quantification procedure, sample preparation procedure, or an antibiotic susceptibility testing (AST) procedure.

As previously discussed, the sample 102 can comprise or refer to a bacterial culture derived from at least one of a sample obtained from a patient or subject, a biological sample, an environmental sample, and a food sample. For example, the sample 102 can comprise or refer to a bacterial culture or a re-suspended bacterial culture derived from a bodily fluid or swab obtained from a patient or subject. As a more specific example, the sample 102 can comprise a bacterial culture or a re-suspended bacterial culture derived from a bodily fluid or swab obtained from a patient or subject that has tested positive for microorganism growth.

More specifically, the sample 102 can comprise a bacterial culture derived from blood obtained from a patient or subject that has tested positive for microorganism growth. In some embodiments, the sample 102 can be or refer to a positive blood culture. For purposes of this disclosure, a positive blood culture can be a bacterial culture derived from blood drawn from a patient or subject that has tested positive for bacterial growth.

In some embodiments, an aqueous growth media can be added to the sample 102 to dilute the sample 102 prior to being introduced into the sample container 802. In other embodiments, the aqueous growth media can be added to the sample 102 once the sample 102 has been injected, delivered, or otherwise introduced into the sample container 802.

In one embodiment, the aqueous growth media can be a glucose supplemented Mueller Hinton broth (MHG). In other embodiments, the aqueous growth media can be a solution containing bacto-tryptone, tryptic soy digest, yeast extract, beef extract, cation-adjusted Mueller Hinton Broth (CAMHB), starch, acid hydrolysate of casein, calcium chloride, magnesium chloride, sodium chloride, blood or lysed blood including lysed horse blood (LHB), CAMHB-LHB, glucose or other carbohydrates, or a combination thereof.

The microorganisms or infectious agents that can be assayed using the sensor apparatus 800 can be any metabolizing single- or multi-cellular organism including any of the species or genus of bacteria and fungi previously described.

The sample container 802, the container cap 806, or a combination thereof can be made in part or be fabricated from a non-conducting material. The sample container 802, the container cap 806, or a combination thereof can be made in part or be fabricated from a non-leaching or sterilizable material. The sample container 802, the container cap 806, or a combination thereof can be made in part or be fabricated from a polymeric material (e.g., a thermoplastic, a cured photopolymer, or a combination thereof), a ceramic material or glass, or a combination thereof. For example, the sample container 802, the container cap 806, or a combination thereof can be made in part or be fabricated from polycarbonate, polypropylene (PP), nylon, acrylonitrile butadiene styrene (ABS), polyethylene (PE), polystyrene (PS), polyvinyl chloride (PVC), poly(methyl methacrylate) (PMMA), polydimethylsiloxane (PDMS), or a combination thereof. As a more specific example, the sample container 802, the container cap 806, or a combination thereof can be made in part of molded polycarbonate or a cured low viscosity liquid photopolymer such as Somos® WaterShed XC.

FIG. 9A illustrates a side cross-sectional view of the sensor apparatus 800. As shown in FIG. 9A, the sensor apparatus 800 can comprise a reference sensor component 804 fabricated as a container cap 806 and a sample container 802. The container cap 806 can be removably or detachably coupled or fastened to the sample container 802.

The reference sensor component 804 can comprise a reference conduit 900 comprising a reference conduit cavity 902, a reference conduit first opening 904, and a reference conduit second opening 906. The reference conduit 900 can be an elongate channel or passageway configured to extend into a sample chamber 908 of the sample container 802.

The sensor apparatus 800 can also comprise a wicking component 910 positioned within the reference conduit cavity 902 and extending through a length of the reference conduit cavity 902. In some embodiments, the wicking component 910 can fill up or occupy all of the space within the reference conduit cavity 902. In other embodiments, the wicking component 910 can partially fill up or partially occupy the space within the reference conduit cavity 902.

The wicking component 910 can have a wick distal end 912 and a wick proximal end 914. At least part of the wicking component 910 can be in fluid communication with the sample chamber 908 such that when the reference sensor component 804 (e.g., the container cap 806) is attached, fastened, or coupled to the sample container 802 at least some of the sample 102 in the sample chamber 908 is drawn up, absorbed, or otherwise wicked by at least a portion of the wick distal end 912 in a direction of the wick proximal end 914.

In some embodiments, at least part of the wick distal end 912 can extend past the reference conduit second opening 906 such that the wick distal end 912 protrudes or extends into the sample chamber 908. In these embodiments, the wick distal end 912 extends or protrudes into the fluid sample 102 when the sample chamber 908 is filled by the sample 102.

In other embodiments, the entire wick distal end 912 is positioned proximal or above the reference conduit second opening 906 such that the wick distal end 912 does not protrude or extend into the sample chamber 908. In these embodiments, the wick distal end 912 can still be in fluid communication with the sample chamber 908 and the fluid sample 102 can still reach or contact the wick distal end 912 by being drawn up into the reference conduit 900 by capillary action or by perturbing/shaking the sample container 802.

FIG. 9A also illustrates that the reference conduit 900 can be tapered such that a volume of the reference conduit cavity 902 tapers or narrows from the reference conduit first opening 904 to the reference conduit second opening 906. The shape of the wicking component 910 can match or accommodate the shape of the reference conduit cavity 902. The wicking component 910 can be configured such that the shape of the wicking component 910 tapers or narrows from the wick proximal end 914 to the wick distal end 912.

The wicking component 910 can be made in part of a porous material. The wicking component 910 can be made in part of a material comprising pores sized between 15 μm to about 150 μm (e.g., about 50 μm).

In some embodiments, the wicking component 910 can be made in part of a polymeric material. As a more specific example, the wicking component 910 can be made in part of a porous polymeric material comprising pores sized between 15 μm to about 150 μm. In one embodiment, the wicking component 910 can be made in part of high-density polyethylene (HDPE). For example, the wicking component 910 can be made in part of HDPE having pores sized about 50 μm.

In other embodiments, the wicking component 910 can be made in part of natural fibers. For example, the wicking component 910 can be made in part of cellulose fibers, pulp, paper, cotton, or a combination thereof.

The wicking component 910 can also be treated by a surfactant such that at least a surface of the wicking component 910 is covered by the surfactant. In some embodiments, the wicking component 910 can be saturated by the surfactant or immersed in a solution comprising the surfactant prior to being introduced into the reference conduit cavity 902. The surfactant can be configured to increase a hydrophilicity of the wicking component 910 (i.e., to make a substantially hydrophobic surface of the wicking component 910 more hydrophilic). In some embodiments, the surfactant can be a fluorosurfactant. In other embodiments, the surfactant can be a non-ionic surfactant such as one or more Poloxamers. As a more specific example, the surfactant can comprise Pluronic® F-68.

The reference sensor component 804 can also comprise a reference electrode material 808 disposed at the wick proximal end 914. The reference electrode material 808 can be an electrically-conductive material applied or dispensed on the wick proximal end 914.

In some embodiments, the reference electrode material 808 can be an electrically-conductive ink applied or dispensed on the wick proximal end 914. The electrically-conductive ink applied or dispensed on the wick proximal end 914 can be hardened by curing. More specifically, the electrically-conductive ink can be a silver-silver chloride (Ag—AgCl) ink.

At least part of the reference electrode material 808 can be in physical contact with the wicking component 910. In some embodiments, at least part of the reference electrode material 808 can protrude or extend beyond the container cap 806. The reference electrode material 808 can be a cured and hardened mass positioned at the wick proximal end 914. In certain embodiments, the reference electrode material 808 can be positioned in the middle of the container cap 806.

One advantage of the wicking component 910 disclosed herein is that the wicking component 910 can draw up the liquid sample 102 and the sample 102 can advance by capillary action through the pores of the wicking component 910 toward the reference electrode material 808. For example, the liquid sample 102 is wicked to the wick proximal end 914 where it makes fluid contact with the reference electrode material 808.

When the reference electrode material 808 is made of a material such as silver-silver chloride (Ag—AgCl), the wicking component 910 can also act as a barrier or hindrance to silver ions ($Ag^+$) that would otherwise diffuse freely into the sample 102. Such silver ions can be harmful to or otherwise affect the growth of the microorganisms or infectious agents in the sample 102. The wicking component 910 can act as a barrier or hindrance to the harmful silver ions by slowing down or stalling the diffusion of such ions into the sample 102. The wicking component 910 having the dimensions and shape disclosed herein can be effective in slowing down or stalling the diffusion of such harmful ions.

The reference sensor component 804 can be electrically coupled by conductive connections 134 to a parameter analyzer 916. The parameter analyzer 916 can be a voltmeter or a multimeter. For example, the parameter analyzer 916 can be a high-impedance voltmeter such as voltmeter 136 discussed previously.

The sensor apparatus 800 can also comprise an active sensor component 816 attached to or otherwise positioned along a container wall 814 of the sample container 802. In other embodiments not shown in the figures, the active sensor component 816 can be attached or otherwise positioned along a bottom of the sample container 802.

The active sensor component 816 can comprise an active electrode material 918, an active electrode housing 920, and a conductive contact layer 922. At least part of the active electrode material 918 can be in fluid communication with the sample chamber 908. For example, at least part of the active electrode material 918 can extend or protrude into the sample chamber 908. The active electrode material 918 can be positioned such that at least a layer or surface of the active electrode material 918 is in fluid contact with the sample 102 when the sample chamber 908 is filled at least partly with the sample 102.

The active electrode housing 920 can partially enclose or house the active electrode material 918, the conductive contact layer 922, or a combination thereof. The active electrode housing 920 can be made of an inert non-conductive material. In some embodiments, the active electrode housing 920 is made of the same material as the container walls 814 and is a molded feature of the container walls 814. The active electrode housing 920 can be a conduit or channel defined along a container wall 814 of the sample container 802. In other embodiments, the active electrode housing 920 can be defined along a bottom of the sample container 802. The active electrode housing 920 can expose at least part of the active electrode material 918 at one end of the active electrode housing 920 and at least part of the conductive contact layer 922 at another end of the active electrode housing 920. In certain embodiments, one or more conductive connections 134 can make physical contact with the conductive contact layer 922 or the active electrode material 918 through the active electrode housing 920.

The conductive contact layer 922 can be coupled to the active electrode material 918 and positioned or otherwise disposed proximal to or radially outward of the active electrode material 918 (e.g., closer toward an exterior of the sample container 802). The conductive contact layer 922 can be made in part of one or more metals. In some embodiments, the conductive contact layer 922 can be made in part of aluminum (Al), copper (Cu), platinum (Pt), or a combination thereof. The conductive contact layer 922 can be electrically coupled to the reference electrode material 808 by conductive connections 134 via the parameter analyzer 916. The conductive connections 134 can be made in part of a conductive material. The conductive connections 134 can be conductive wires or conductive traces. In one embodiment, the conductive connections 134 can be copper wires or copper traces. For example, the conductive connections 134 can be electro-deposited copper, rolled annealed copper, high-ductility electro-deposited copper, or a combination thereof. In other embodiments, the conductive connections 134 can be made in part of silver or nickel. The conductive connections 134 can be brought into contact with the reference sensor component 804 and the active sensor component 816 once the sample container 802 is filled, at least partially, with the sample 102.

The solution characteristic of the sample 102 can be determined based on a potential difference measured between the active electrode material 918 and the reference electrode material 808. The reference electrode material 808 can act as a reference electrode and provide a stable half-cell potential compared to the active electrode material 918 and a potential difference between the active electrode and the reference electrode can be used to determine the pH or ORP of the sample 102. For example, the reference electrode material 808 (e.g., the Ag—AgCl ink) can be configured to exhibit a substantially stable electrode potential compared to the active electrode material 918 when the active electrode material 918 is in electrical communication with the reference electrode material 808.

In some embodiments, the solution characteristic measured or monitored can be a pH of the sample 102. In other embodiments, the solution characteristic measured or monitored can be an oxidation reduction potential (ORP) of the sample 102.

When the solution characteristic measured or monitored is pH, the active electrode material 918 can be a pH-sensitive material. The pH-sensitive material can be or comprise any of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

When the solution characteristic measured or monitored is ORP, the active electrode material 918 can be a redox-sensitive material. The redox-sensitive material can be or comprise any of platinum (Pt), gold (Au), a redox sensitive metal oxide, or a combination thereof. More specifically, the redox-sensitive material can be or comprise any of silicon dioxide ($SiO_2$), aluminum oxide ($Al_2O_3$), titanium dioxide ($TiO_2$), tantalum pentoxide ($Ta_2O_5$), hafnium dioxide ($HfO_2$), iridium dioxide ($IrO_2$), ruthenium dioxide ($RuO_2$), zirconium dioxide ($ZrO_2$), or a combination thereof.

As illustrated in FIG. 9A, when the reference sensor component 804 is implemented as a container cap 806, the container cap 806 can have dimensions as defined by a cap width 924 (or diameter) and a cap height 926. In some embodiments, the cap width 924 can be between about 10.0 mm to about 20.0 mm. For example, the cap width 924 can be about 15.7 mm. In some embodiments, the cap height 926 can be between about 5.0 mm to about 20.0 mm. For example, the cap height 926 can be about 10.5 mm. When the container cap 806 is fastened, affixed, or otherwise coupled to the sample container 802, the sensor apparatus 800 can have an apparatus height 928 as measured from a bottom of the sample container 802 to the cap top 810 of the container cap 806.

In some embodiments, the apparatus height 928 can be between about 20.0 mm to about 50.0 mm. In other embodiments, the apparatus height 928 can be between about 25.0 mm to about 35.0 mm. For example, the apparatus height 928 can be about 31.3 mm.

As illustrated in FIG. 9A, the wicking component 910 can have a wick height 930 as measured from the wick proximal end 914 to the wick distal end 912. In some embodiments, the wick height 930 can be between about 10.0 mm to about 20.0 mm. More specifically, the wick height 930 can be between about 14.0 mm to about 15.0 mm. For example, the wick height 930 can be about 14.8 mm.

One advantage of a wicking component 910 having the wick height 930 disclosed herein is that such a wicking component 910 can allow sufficient amounts of the sample 102 to be drawn up in the direction of the reference electrode material 808 while still acting as a barrier or impediment to certain harmful ions (e.g., silver ions) that flow from the reference electrode material 808 toward the microbial-laden sample 102 in the sample chamber 908.

FIG. 9A also illustrates that the reference electrode material 808 can have a reference material height 932 (or thickness) and a reference material width 934 (or diameter). When the reference electrode material is a cured and hardened mass of silver-silver chloride (Ag—AgCl), the reference material height 932 and the reference material width 934 can be the height and width, respectively, of the hardened mass of silver-silver chloride.

In some embodiments, the reference material height 932 can be between about 0.2 mm and 1.0 mm. For example, the reference material height 932 can be about 0.4 mm. In some embodiments, the reference material width 934 can be between about 2.0 mm to about 5.0 mm. For example, the reference material width 934 can be about 3.0 mm. One advantage of the reference electrode material 808 disclosed herein is that the reference electrode material 808 can act as a stable reference electrode or provide a stable reference potential for up to 10-hours of testing or operation.

As illustrated in FIG. 9A, the reference electrode material 808 can be positioned or disposed, at least partially, within a divot, depression, or concave region created by the wicking component 910 and the reference conduit 900. When the reference electrode material 808 is a cured or hardened electrically-conductive ink or solution (e.g., Ag—AgCl ink), the divot, depression, or concave region can act as a receiving space for the liquid ink or solution to be cured.

FIG. 9A also illustrates that the sensor apparatus 800 can comprise an aeration port 936 defined along a bottom side of the sample container 802, a container wall 814 of the sample container 802, or a combination thereof. The aeration port 936 can be covered by a first air-permeable membrane 938. The aeration port 936 and the first air-permeable membrane 938 can be configured to allow a gas 940 to enter the sample chamber 908. In some embodiments, the gas 940 can be ambient air (e.g., the air in a laboratory, clinical setting, or testing facility). In other embodiments, the gas 940 can comprise a combination of pressurized oxygen, carbon dioxide, nitrogen, and argon. The aeration port 936 and the first air-permeable membrane 938 can allow air to enter the sample chamber 908 through the aeration port 936 and the first air-permeable membrane 938 to aerate the sample 102 in the sample chamber 908. Aerating the sample 102 can benefit aerobic organisms such as *Pseudomonas aeruginosa* or *Acinetobacter baumanii* by providing an oxygen rich environment within the sample chamber 908. Aerating the sample 102 can accelerate the growth of a microbial population within the sample 102.

The aeration port 936 can be an opening or channel defined along the bottom side of the sample container 802, the container wall 814 of the sample container 802, or a combination thereof. For example, the aeration port 936 can be defined in the middle or center of the container bottom.

In additional embodiments, the aeration port 936 can be defined along a cap top 810 of the container cap 806 and the gas 940 can be pumped into the sample chamber 908 from the top of the sample container 802.

The gas 940 (e.g., ambient air) can be pumped into the sample chamber 908 by a micropump or another pump-type device. The gas 940 (e.g., ambient air) can be pumped or otherwise directed into the sample chamber 908 through the aeration port 936 and the first air-permeable membrane 938 at a constant flow rate of between about 1.0 and 10.0 mL/min. In other embodiments, the gas 940 (e.g., ambient air) can be pumped or otherwise directed into the sample chamber 908 through the aeration port 936 and the first air-permeable membrane 938 at specific duty cycles or intervals.

FIG. 9A also illustrates that a second air-permeable membrane 942 can cover at least part of an underside of the container cap 806. The second air-permeable membrane 942 can allow any gas 940 pumped or otherwise introduced into the sample chamber 908 to exit the sample chamber 908 while also preventing any liquid within the sample chamber 908 to spill out of the sample container 802. The second air-permeable membrane 942 can also allow any gaseous byproducts generated or created within the sample chamber 908 from exiting the sample chamber 908.

In some embodiments, the first air-permeable membrane 938 and the second air-permeable membrane 942 are made of the same material. The first air-permeable membrane 938 and the second air-permeable membrane 942 can be made of a hydrophobic air-permeable film or thin-sheet. For example, the first air-permeable membrane 938 and the second air-permeable membrane 942 can both be made of or comprise polytetrafluoroethylene (PTFE).

As shown in FIG. 9A, the container cap 806 can be removably or detachably coupled or fastened to the sample container 802 by being screwed on to a proximal portion of the sample container 802 via a threaded connection 944. When the container cap 806 (serving as part of the reference sensor component 804) is fastened or coupled to the sample container 802 by the threaded connection 944, an airflow pathway 946 can be created as air enters the aeration port 936 through the first air-permeable membrane 938 into the sample chamber 908 and exits the sample chamber 908 through the second air-permeable membrane 942 and air gaps 948 defined in between the threads of the container cap 806 and the sample container 802.

FIG. 9B illustrates an embodiment of a reference sensor component 804 of the sensor apparatus 800. As shown in FIG. 9B, the reference sensor component 804 can be implemented or fabricated as a container cap 806 comprising a reference conduit 900 extending from an underside 950 of the container cap 806. The reference conduit 900 can be an elongate channel extending from the underside 950 of the container cap 806. The reference conduit 900 can be hollow and can be defined by a reference conduit cavity 902 extending from a reference conduit first opening 904 to a reference conduit second opening 906.

The reference conduit cavity 902 can extend through the entire length of the reference conduit 900. The reference conduit cavity 902 can be substantially shaped as a cylinder, an elongate conic, an elongate frustoconic, an elongate cuboid, or a combination thereof. The shape of the wicking component 910 can accommodate and match the shape of the reference conduit cavity 902.

The container cap 806 can be made in part of a transparent or clear material or a transparent or clear non-conducting material. In other embodiments, the container cap 806 can be made in part of a translucent or see-through material. For example, as shown in FIG. 9B, at least part of the wicking component 910 can be visible through the lateral sides 812 of the container cap 806. This can allow a user or operator of the sensor apparatus 800 to observe the wicking of the fluid sample 102 from the wick distal end 912 to the wick proximal end 914 when the container cap 806 is fastened to the sample container 802 and ensure that at least some of the sample 102 is able to reach the reference electrode material 808 at the wick proximal end 914. In some embodiments, the container cap 806 can be made in part of a clear or transparent polymeric material, glass, or a combination thereof.

A method of manufacturing the reference sensor component 804 can comprise providing a container cap 806 configured to be removably coupled to a sample container 802. The sample container 802 can be configured to receive the sample 102. As previously discussed, a reference conduit 900 can extend from the underside 950 of the container cap 806. The reference conduit 900 can comprise a reference conduit cavity 902. In these and other embodiments, the method can also comprise molding a reference sensor component 804 in the shape of a container cap 806 having a reference conduit 900 defined in a center of the container cap 806. For example, the container cap 806 can be molded through injection molding or cast molding. In other embodiments, the method can comprise 3D-printing a container cap 806 having a reference conduit 900 defined in a center of the container cap 806 and having a reference conduit cavity 902 extending through a length of the reference conduit 900.

The method can further comprise placing or positioning a wicking component 910 into the reference conduit cavity 902 of the reference conduit 900. The wicking component 910 can comprise a wick distal end 912 and a wick proximal end 914. For example, the wicking component 910 can be made in part of a porous polymeric material (e.g., HDPE), natural fibers, or a combination thereof. The wicking component 910 can also be treated, immersed, or otherwise saturated with a surfactant prior to being introduced or placed into the reference conduit cavity 902.

In some embodiments, grooves or furrows can be created on the surface of the wicking component 910, the reference electrode material 808 (e.g., the cured electrically-conductive ink), or a combination thereof. Increasing the surface area of the wicking component 910, the reference electrode material 808, or a combination thereof can improve the stability of the half-cell potential of the reference electrode.

The method can also comprise applying or dispensing an electrically-conductive ink (e.g., Ag—AgCl ink) on the wick proximal end 914. The electrically-conductive ink can be dispensed or otherwise applied to the wick proximal end 914 via a syringe, a dropper, a droplet dispenser, or a pipette. The electrically-conductive ink can be dispensed or otherwise applied to a divot, groove, or depression defined by the wick proximal end 914 and a segment of the reference conduit 900 surrounding the wick proximal end 914.

Dispensing the electrically-conductive ink can further comprise dispensing between about 50 µL and about 500 µL of the electrically-conductive ink on the wick proximal end 914. More specifically, dispensing the electrically-conductive ink can further comprise dispensing between about 80 µL and about 120 µL of the electrically-conductive ink on the wick proximal end 914. For example, the method can comprise dispensing about 100 µL of the electrically-conductive ink on the wick proximal end 914.

The electrically-conductive ink can then be cured until the electrically-conductive ink hardens to become the reference electrode material 808. In some embodiments, the method can involve curing the electrically-conductive ink at a temperature above 100° C. More specifically, the method can involve curing the electrically-conductive ink at a temperature between about 110° C. and 120° C. For example, the method can involve curing the electrically-conductive ink at 115° C. The electrically-conductive ink can be cured for a period of time between about 60 minutes and about 180 minutes to harden the electrically-conductive ink. For example, the electrically-conductive ink can be cured for a period of time between about 110 minutes and about 130 minutes. For example, the electrically-conductive ink can be cured for 120 minutes. More specifically, the electrically-conductive ink can be cured for 120 minutes at 115° C.

A method of measuring a solution characteristic of the sample 102 can comprise filling the sample chamber 908 of the sample container 802 with the sample 102. The sample 102 can comprise an infectious agent or microorganisms. The method can also involve attaching a reference sensor component 804 configured as a container cap 806 to the sample container 802.

The container cap 806 can comprise the reference conduit 900 comprising the reference conduit cavity 902, the reference conduit first opening 904, and the reference conduit second opening 906. The reference conduit cavity 902 can be filled in part by a wicking component 910 extending through the reference conduit cavity 902 having a wick distal end 912 and a wick proximal end 914.

At least part of the wicking component 910 can be in fluid contact with the sample 102 in the sample chamber. At least some of the sample 102 can be drawn up by the wicking component 910 in a direction of the wick proximal end 914. A reference electrode material 808 (e.g., a cured and hardened electrically-conductive ink) can be disposed at the wick proximal end 914. The method can further comprise electrically coupling the reference electrode material 808 to a parameter analyzer 916 (e.g., a high-impedance voltmeter) and electrically coupling the parameter analyzer 916 to an active sensor component 816 comprising an active electrode material 918. At least part of the active electrode material 918 can extend into the sample chamber 908 and be in fluid contact with the sample 102 in the sample chamber 908. When the wicking component 910 draws or wicks up the sample 102, the sample 102 can reach the reference electrode material 808 and charge carriers within the sample 102 can establish an electrical connection between the reference electrode material 808 and the active electrode material 918. At this point, an electrical circuit is formed which can then be used to conduct measurements of potential changes in the sample 102.

The method can further comprise determining the solution characteristic of the sample 102 based on a potential difference measured between the active electrode material 918 and the reference electrode material 808. As previously discussed, the solution characteristic measured can be a pH of the sample 102, an ORP of the sample 102, or a combination thereof.

The method can also comprise pumping air into the sample chamber 908 through an aeration port 936 defined along at least one of a bottom side and a lateral side of the sample container 802. A hydrophobic air-permeable membrane (e.g., the first air-permeable membrane 938) can cover the aeration port 936. The air pumped into the sample chamber 908 can aerate the sample 102 and accelerate the growth of the infectious agents or microorganisms within the sample 102.

The air pumped into the sample chamber 908 can also exit the sample chamber 908 through an additional air-permeable membrane (e.g., the second air-permeable membrane 942) covering at least part of an underside 950 of the container cap 806 and, eventually, through air gaps 948 (see FIG. 9A) defined in between the container cap 806 and the sample container 802 (e.g., through air gaps 948 defined in between male threads of the sample container 802 and female threads of the container cap 806).

Figure 10:
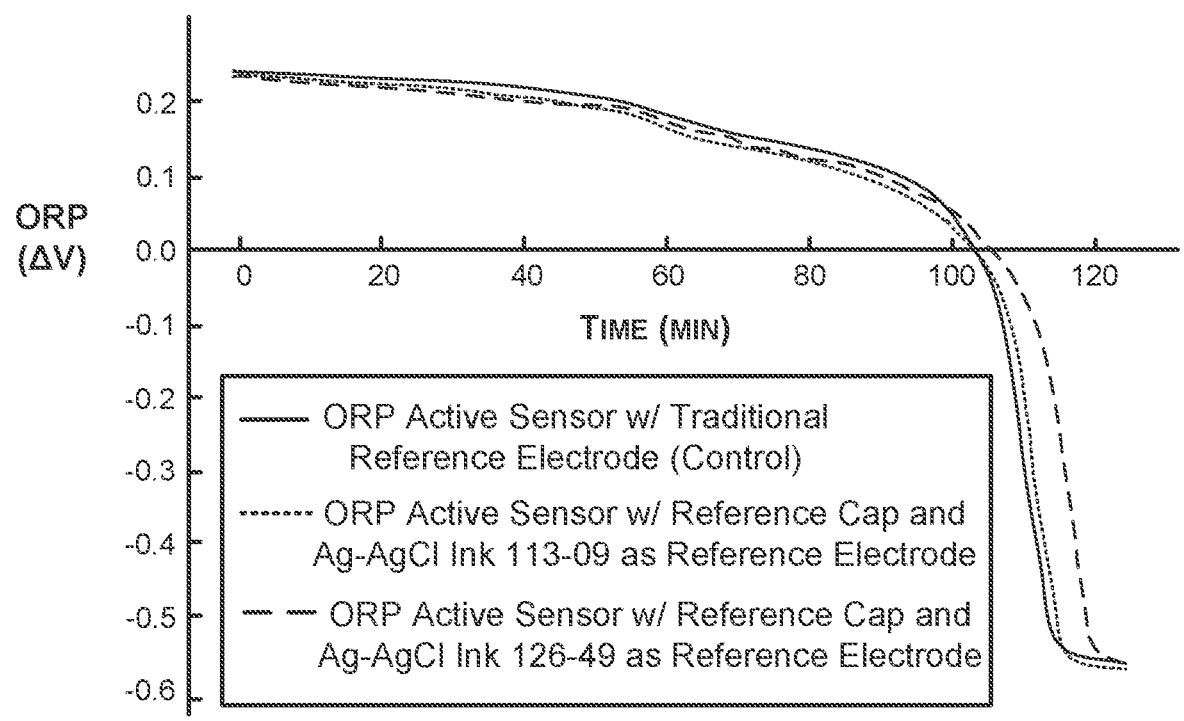
FIG. 10 illustrates a change in oxidation reduction potential (ORP) of three aliquots of a sample measured over time using three different sensor setups.

FIG. 10 illustrates a change in oxidation reduction potential (ORP) of three aliquots of a sample 102 measured over time using three different sensor setups. All such samples contained the bacteria *Escherichia coli* (*E. coli* or ECo). One such sensor setup involved an active sensor component 816 comprising a redox-sensitive material as the active electrode material 918 (e.g., an ORP active sensor) and a commercial off-the-shelf silver-silver chloride reference electrode. This sensor setup served as a control and the results obtained from these measurements served as a standard or benchmark for other measurements of *E. coli* bacterial growth. The other two sensor setups involved the same active sensor component 816 comprising the redox-sensitive material as the active electrode material but used the container cap 806 disclosed herein as the reference sensor component 804. In these instances where the container cap 806 served as the reference sensor component 804, the reference electrode material 808 was a cured and hardened deposit of silver-silver chloride (Ag—AgCl) ink. In one such sensor setup, the Ag—AgCl ink used was Ag—AgCl 113-09 developed by Creative Materials Inc. In the other sensor setup, the Ag—AgCl ink used was Ag—AgCl 126-49 developed by Creative Materials Inc.

As shown by the three *E. coli* growth curves, the two sensor setups utilizing the container cap 806 as the reference sensor component 804 performed similar to the sensor setup utilizing the traditional commercial off-the-shelf silver-silver chloride reference electrode. Any variations in the signal timing were within acceptable ranges based on the active sensor used.

Figure 11:
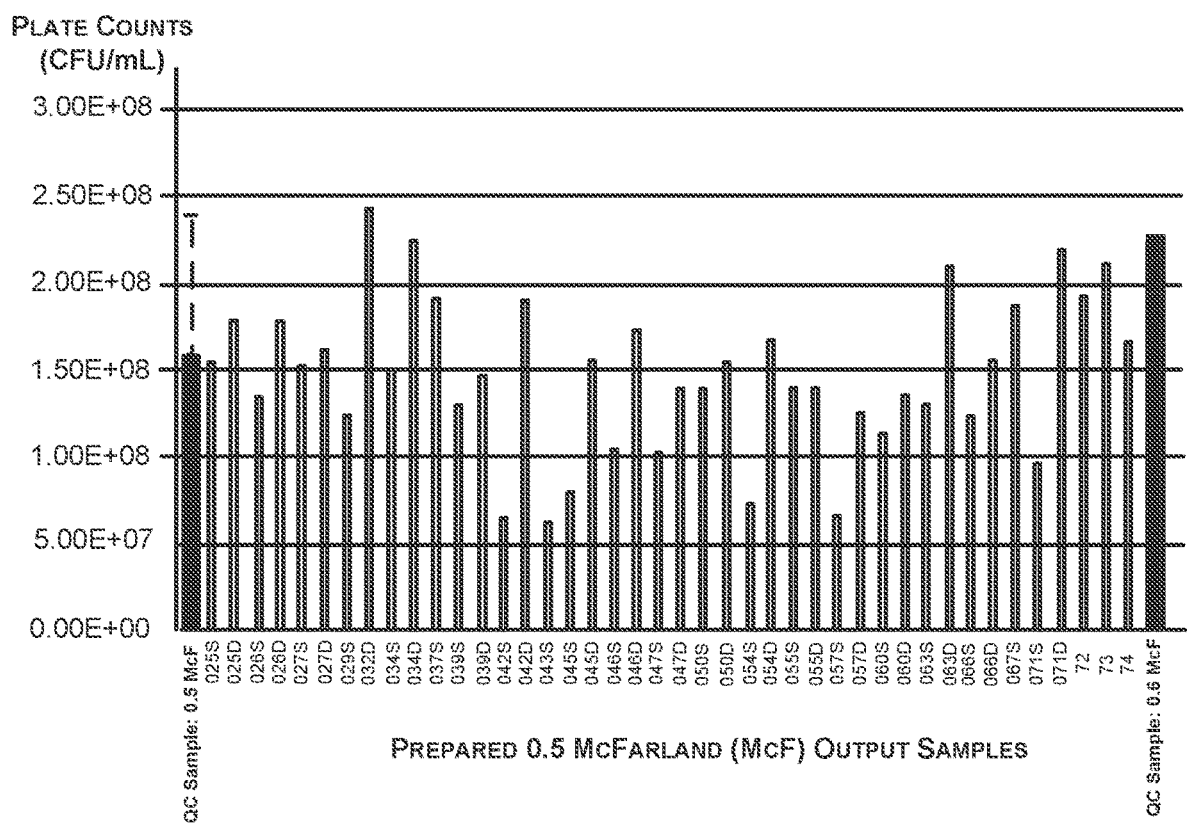
FIG. 11 illustrates the results of cell counts conducted on plated bacterial colonies of output samples comprising various strains of *E. coli*.

FIG. 11 is a graph illustrating the results of cell counts (represented as colony-forming units (CFU) per mL) conducted on plated bacterial colonies of output samples comprising various strains of *E. coli*. In some embodiments, the sensor apparatus 800 disclosed herein can be used as part of a system for preparing an output sample of a defined microorganism concentration. For example, the sensor apparatus 800 disclosed herein can be used as part of a system for preparing an output sample of a defined microorganism concentration, such as 0.5 McFarland (McF) to 0.6 McF (a microorganism suspension exhibiting a turbidity equivalent to 0.5 McF to 0.6 McF), commonly used as an input for antibiotic susceptibility testing.

The dark colored bars in FIG. 11 represent quality control (QC) samples exhibiting a turbidity of 0.5 McF and 0.6 McF as measured by a standard turbidity (optical density) meter. The QC samples were prepared by resuspending colonies from an 18-24 hour culture plate into saline to a final concentration between about 0.5 McF and 0.6 McF (a concentration between about 0.5 McF to 0.6 McF is the acceptable input concentration for an antibiotic susceptibility test). The QC samples comprised a quality control strain of *E. coli* known as ATCC 25922. Once the turbidity levels of such QC samples reached 0.5 McF and 0.6 McF, such samples were then plated and a viable cell count conducted on such plated samples (the results of such counts are presented in units of CFU/mL on the graph).

The various white-colored bars in FIG. 11 represent cells counts conducted on output samples of a defined concentration prepared using the sensor apparatus 800 disclosed herein. The output samples were prepared from source samples comprising *E. coli* of various strains from positive blood cultures from patients with sepsis. A defined concentration of approximately $1.50*10^8$ CFU/mL (exhibiting a turbidity of 0.5 McF) was set as the goal for all such output samples.

Source samples comprising *E. coli* of various strains were introduced into the sample chambers 908 of sample containers 802 disclosed herein. Reference sensor components 804 (e.g., container caps 806) were then fastened to such sample containers 802 and a change in the solution characteristic of such samples were then measured or monitored over time by the parameter analyzer 916.

The system can also comprise one or more computing devices communicatively coupled to the parameter analyzer 916. The one or more computing devices can retrieve certain look-up tables associated with a particular infectious agent species (i.e., a species-specific look-up table) or an interspecies or universal look-up table to determine a real-time concentration of the infectious agent within the sample chamber 908 based on a change in the solution characteristic of the sample within the sample chamber 908.

In some embodiments, concentration data can be determined directly from one or more look-up tables based on real-time changes in the solution characteristic monitored or measured by the parameter analyzer 916, the one or more computing devices, or a combination thereof. In these embodiments, a real-time change in the solution characteristic of the sample within the sample chamber 908 can be directly mapped to a threshold solution characteristic change in a look-up table, which can directly relate to an estimated concentration of the infectious agent within the sample chamber 908.

In other embodiments, additional calculations and data interpolations can be performed by the one or more computing devices based on threshold data from one or more look-up tables and real-time solution characteristic changes measured or monitored by the sensor apparatus 800. For example, one method of preparing an output sample of a defined concentration can comprise calculating a sample incubation or sample preparation time corresponding to the amount of time necessary for the infectious agent within the sample chamber 908 to reach the defined concentration based on a first threshold time, a second threshold time, concentration data from at least one look-up table, and the defined concentration desired. This method is further described in U.S. patent application Ser. No. 16/430,266, the content of which is incorporated herein by reference in its entirety.

As can be seen in FIG. 11, plated cell counts conducted on output samples (of 0.5 McF) generated in part with the sensor apparatus 800 disclosed herein compared favorably to the 0.5 McF and 0.6 McF QC samples generated using the "gold-standard" of resuspending colonies from an 18 to 24 hour culture plate and determining the concentration of such suspensions using optical density measurements. Almost all output samples prepared using the sensor apparatus 800 and methods disclosed herein resulted in samples having an infectious agent concentration within an acceptable range of the QC samples. FIG. 11 illustrates that the sensor apparatus 800 and methods disclosed herein can be used to effectively generate output samples of a defined concentration (e.g., a 0.5 McF bacterial sample).

Figure 12:
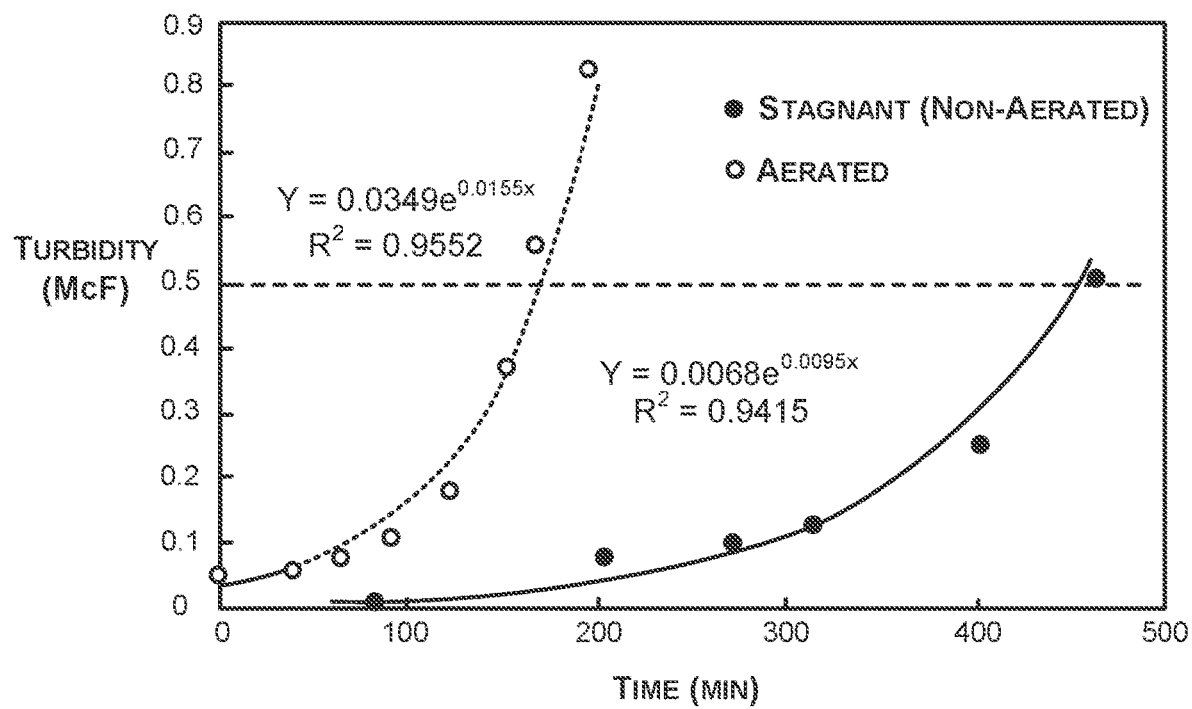
FIG. 12 illustrates the effects of aeration on growth rates of two samples comprising the bacteria *Pseudomonas aeruginosa*

FIG. 12 illustrates the effects of aeration on growth rates of two samples 102 comprising the aerobic bacteria *Pseudomonas aeruginosa* (PAe). Growth rates were measured based on the turbidity of the samples 102 over time (with turbidity determined based on the McFarland (McF) reference standard for representing the turbidity of bacterial suspensions). The more turbid the sample solution, the higher the concentration of PAe within the sample 102.

As shown in FIG. 12, aerating the sample 102 (as shown by the plot in broken lines) increased the growth rate of the bacteria within the sample 102 such that the time it took for the sample 102 to reach a turbidity level equivalent to 0.5 McFarland (McF) decreased significantly (180 minutes versus 460 minutes) compared to the non-aerated or stagnant sample 102 (as shown by the solid-line plot). The sample 102 can be aerated by pumping gas (e.g., ambient air, oxygen, etc.) into the sample chamber 908 through the aeration port 936 and the air-permeable membrane 938. In some embodiments, the aeration port 936 can be defined on a bottom side of the sample container 802. The gas 940 or ambient air can be pumped into the sample chamber 908 using a micropump. In some embodiments, the gas 940 or ambient air can be pumped into the sample chamber 908 at a constant flow rate between about 1 mL/min to about 10 mL/min.

Figure 13:
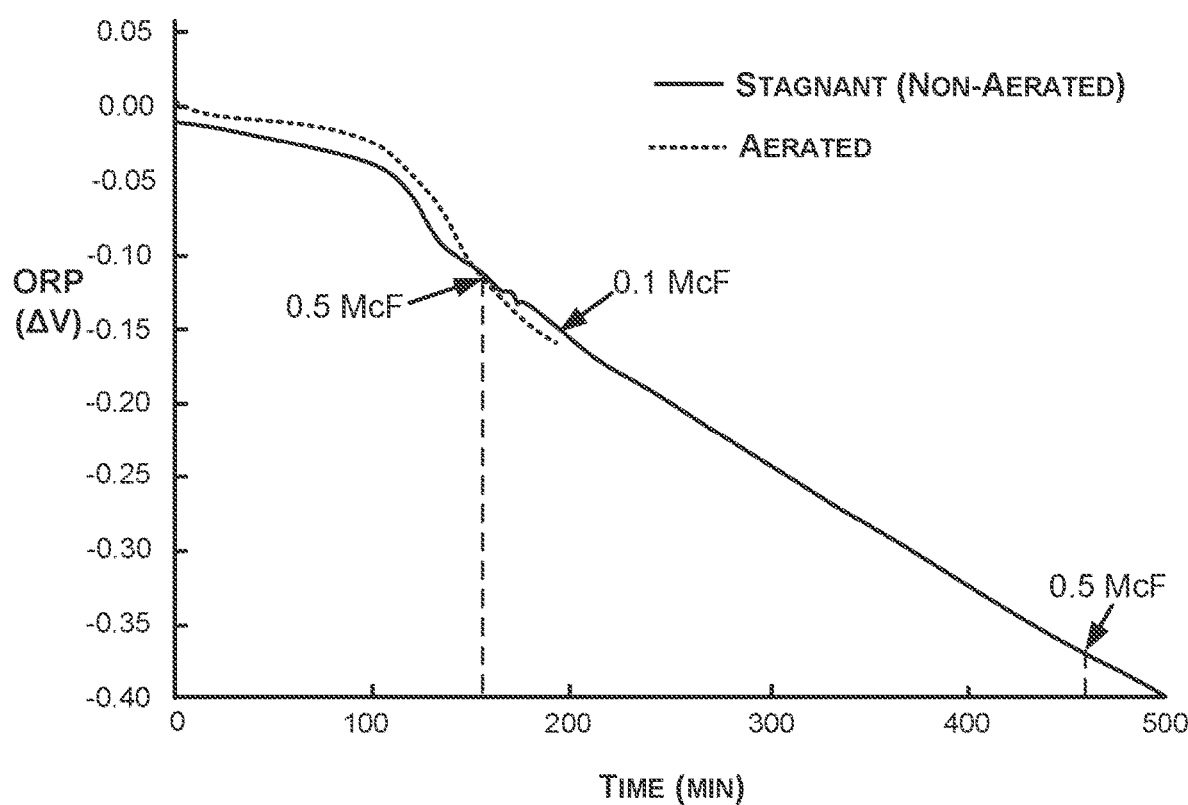
FIG. 13 illustrates the effects of aeration on the preparation time of two 0.5 McFarland bacterial samples using the sensor apparatus.

FIG. 13 illustrates the effects of aeration on the preparation time of two 0.5 McFarland bacterial samples using the sensor apparatus 800 disclosed herein. Such 0.5 McFarland samples could be prepared for further downstream testing such as part of one or more antibiotic susceptibility tests.

As shown in FIG. 13, one sample container 802 filled with a sample comprising *Pseudomonas aeruginosa* (PAe) was aerated (with, for example, ambient air) while another sample container 802 filled with a similar sample comprising PAe was not aerated. A container cap 806 serving as the reference sensor component 804 was then fastened to each of the sample containers 802 and each sensor apparatus 800 was then electrically coupled to a parameter analyzer 916 used to detect the change in ORP of the sample A computing device or another device coupled to the parameter analyzer 916 then recorded the change in the ORP of the sample within each of the sample containers 802 and compared these values to data within one or more look-up tables retrieved from a computing device coupled to the parameter analyzer 916 or a database accessible by the computing device.

As shown in FIG. 13, the concentration of PAe within the aerated sample container 802 reached a defined concentration of 0.5 McFarland in approximately 160 minutes while the concentration of PAe within the stagnant or non-aerated sample container 802 reached the same defined concentration of 0.5 McFarland in approximately 460 minutes. Thus, it is shown that aerating the sample container 802 significantly enhances bacterial growth rates within the sample chamber 908.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A reference sensor component comprising:
a container cap removably coupled to a sample container configured to receive a sample;
a reference conduit extending from an underside of the container cap, the reference conduit comprising a reference conduit cavity;
an aeration port along a surface of the sample container, the aeration port configured to allow air to enter the sample container;
an air-permeable membrane covering the aeration port;
a wicking component disposed within part of the reference conduit cavity having a wick distal end and a wick proximal end, wherein at least part of the wicking component is configured to be in fluid contact with the sample when the container cap is coupled to the sample container such that at least some of the sample is drawn by the wicking component in a direction of the wick proximal end; and
a reference electrode material disposed at the wick proximal end, wherein the reference electrode material is configured to exhibit a substantially stable electrode potential compared to an active electrode in electrical communication with the reference electrode material.

2. The reference sensor component of claim 1, wherein the container cap is made in part of a non-conducting material.

3. The reference sensor component of claim 2, wherein the container cap is made in part of a transparent non-conducting material such that at least part of the wicking component is visible through the container cap.

4. The reference sensor component of claim 1, wherein the reference electrode material is a cured electrically-conductive ink disposed on the wick proximal end.

5. The reference sensor component of claim 4, wherein the electrically-conductive ink is silver-silver chloride ink.

6. The reference sensor component of claim 4, wherein the electrically-conductive ink has been cured for a period of time between about 60 minutes and about 180 minutes.

7. The reference sensor component of claim 4, wherein a volume of the electrically-conductive ink disposed at the wick proximal end is less than about 500 µL.

8. The reference sensor component of claim 1, wherein the wicking component is made in part of a porous polymeric material.

9. The reference sensor component of claim 1, wherein the wicking component is made in part of natural fibers.

10. The reference sensor component of claim 1, wherein the wicking component comprises pores sized between about 15 µm to about 150 µm.

11. The reference sensor component of claim 1, wherein the wicking component is treated by a surfactant such that at least a surface of the wicking component is covered by the surfactant, wherein the surfactant is configured to increase a hydrophilicity of the wicking component.

12. The reference sensor component of claim 1, wherein the wicking component is made in part of high-density polyethylene (HDPE).

13. The reference sensor component of claim 1, wherein the reference conduit is tapered and wherein the wicking component is shaped such that the wicking component tapers from the wick proximal end to the wick distal end.

* * * * *